US012029834B2

(12) United States Patent
Wadsworth et al.

(10) Patent No.: US 12,029,834 B2
(45) Date of Patent: Jul. 9, 2024

(54) BIOPRINTED MENISCUS IMPLANT AND METHODS OF USING SAME

(71) Applicants: ASPECT BIOSYSTEMS LTD., Vancouver (CA); DEPUY SYNTHES PRODUCTS, INC., Raynham, MA (US)

(72) Inventors: Sam Wadsworth, Vancouver (CA); Simon Beyer, Richmond (CA); Tamer Mohamed, Richmond (CA); Konrad Walus, Vancouver (CA); Mohammad Mostofa Kamal Khan, Vancouver (CA); Elli Kapyla, Vancouver (CA); Julia Hwang, Rayham, MA (US); Joe Ault, Raynham, MA (US)

(*) Notice: Subject to any disclaimer, the term of this patent is extended or adjusted under 35 U.S.C. 154(b) by 948 days.

(21) Appl. No.: 16/956,174

(22) PCT Filed: Dec. 20, 2018

(86) PCT No.: PCT/US2018/066980
§ 371 (c)(1),
(2) Date: Jun. 19, 2020

(87) PCT Pub. No.: WO2019/126600
PCT Pub. Date: Jun. 27, 2019

(65) Prior Publication Data
US 2020/0330647 A1 Oct. 22, 2020

Related U.S. Application Data

(60) Provisional application No. 62/608,523, filed on Dec. 20, 2017.

(51) Int. Cl.
*A61L 27/52* (2006.01)
*A61L 27/26* (2006.01)
*A61L 27/48* (2006.01)

(52) U.S. Cl.
CPC ............. *A61L 27/52* (2013.01); *A61L 27/26* (2013.01); *A61L 27/48* (2013.01); *A61L 2430/06* (2013.01)

(58) Field of Classification Search
CPC .......... A61L 27/52; A61L 27/26; A61L 27/48; A61L 2430/06; A61F 2002/30985; A61F 2/3872
See application file for complete search history.

(56) References Cited

U.S. PATENT DOCUMENTS

| 6,139,574 | A  | 10/2000 | Vacanti et al. |
| 6,733,713 | B2 | 5/2004  | Takahashi |
| 7,051,654 | B2 | 5/2006  | Boland et al. |
| 8,691,274 | B2 | 4/2014  | Xu et al. |
| 8,931,880 | B2 | 1/2015  | Murphy et al. |
| 9,005,972 | B2 | 4/2015  | Xu et al. |
| 9,149,952 | B2 | 10/2015 | Murphy et al. |
| 9,227,339 | B2 | 1/2016  | Murphy et al. |
| 9,301,925 | B2 | 4/2016  | Xu et al. |
| 9,315,043 | B2 | 4/2016  | Murphy et al. |
| 2012/0089238 | A1 | 4/2012 | Hyun-Wook et al. |
| 2013/0164339 | A1 | 6/2013 | Murphy et al. |
| 2013/0345794 | A1 | 12/2013 | Khatiwala et al. |
| 2014/0287960 | A1 | 9/2014 | Shepherd et al. |
| 2016/0009029 | A1 | 1/2016 | Cohen et al. |
| 2017/0202672 | A1 | 7/2017 | Persaud |
| 2017/0348458 | A1 | 12/2017 | Matti et al. |

FOREIGN PATENT DOCUMENTS

| CN | 105477682 A | 4/2016 | |
| EP | 2949350 A1 | 12/2015 | |
| EP | 2310847 B1 | 5/2016 | |
| WO | WO 2007/020449 A2 | 2/2007 | |
| WO | WO 2014/197999 A1 | 12/2014 | |
| WO | WO 2015/026299 A1 | 2/2015 | |
| WO | WO-2015138970 A1 * | 9/2015 | ............ A61L 27/26 |
| WO | WO 2015/148646 A2 | 10/2015 | |
| WO | WO 2016/092106 A1 | 6/2016 | |
| WO | WO 2017/031171 A1 | 2/2017 | |
| WO | WO-2017031171 A1 * | 2/2017 | ............ A61L 27/18 |
| WO | WO 2017/214736 A1 | 12/2017 | |
| WO | WO-2017214736 A1 * | 12/2017 | ............ A61L 27/40 |
| WO | WO 2018/148722 A1 | 8/2018 | |

OTHER PUBLICATIONS

Giri et al. Modified chitosan hydrogels as drug delivery and tissue engineering systems: present status and applications. Acta Pharmaceutica Sinica B. 2012;2(5):439-449.*
U.S. Appl. No. 16/310,341, entitled, "Bioprinted Meniscus Implant and Methods of Using Same", filed Jun. 16, 2018, of Aspect Biosystems Ltd. (Published as U.S. Pat. No. 11,744,919 on Sep. 5, 2023).
U.S. Appl. No. 18/241,754, entitled, "Bioprinted Meniscus Implant and Methods of Using Same", filed Sep. 1, 2023, of Aspect Biosystems Ltd.
Baker, B.M., and Mauck, R. L., "The effect of nanofiber alignment on the maturation of engineered meniscus constructs", Biomaterials, vol. 28(11), pp. 1967-1977 (2007).
Bakarich et al., "Three-dimentional priting fiber reinforced hydrogel composites", ACS Appl. Mater. Interfaces, vol. 6, pp. 15998-16006 (2014).
Chia, H. N. and Hull, M.L., "Compressive Moduli of the Human Medial Meniscus in the Axial and Radial Directions of Equilibrium and at a Physiological Strain Rate", Journal of Orthopaedic Research, vol. 26, Issue 7, pp. 951-956 (2007).
Fithian et al., "Material Properties and Structure-Function Relationships in the Menisci", Clinical Orthopaedics and Related Research, Issue 252, pp. 19-31 (1990).
Jun et al. "Microfluidic spinning of micro-and nano-scale fibers for tissue engineering", Lab on a Chip 14.13, pp. 2145-2160 (2014).
Makris et al., "The knee meniscus: structure-function, pathophysiology, currrent repari techniques, and prosepects for regeneration", Biomaterials, vol. 32(30), pp. 7411-7431 (2011).

(Continued)

*Primary Examiner* — Lynn Y Fan
(74) *Attorney, Agent, or Firm* — Todd Lorenz

(57) ABSTRACT

Provided herein are meniscus implant compositions, as well as method for making and using the same. The subject meniscus implants find use in repairing and/or replacing damaged or diseased meniscal tissue in a mammalian subject.

28 Claims, 15 Drawing Sheets

(56) References Cited

OTHER PUBLICATIONS

Markstedt et al., "3D Bioprinting Human Chondrocytes with Nanocelluslose-Alginate Bioink for Cartilage Tissue Engineering Applications", Biomacromolecules, vol. 16, No. 5, pp. 1489-1496 (2015).

* cited by examiner

| Specimen\Measurement | Peak Contact Pressure (KPa) |
|---|---|
| Bioprinted Meniscus (Alginate) | 13 |
| Animal Meniscus | 160 |
| Bioprinted Meniscus (Alginate + PEGDA 3.4K) | 325 |

FIG. 12

| Printed Material | Secondary material | Toolpath | SPD (20 N) | Indentation (100 kPa) | Tensile (1 MPa) |
|---|---|---|---|---|---|
| 1:1 Chitosan (4.5%) PVA (15%) | PVA (20%) centrifuged | 12% rectilin (vertical/horizontal) | 59 | 110 | 1.51 |
| 1:1 Chitosan (4.5%) PVA (15%) | None | 12% rectilin (vertical/horizontal) | 40.8 | 23.9 | 0.97 |
| None | PVA (20%) | NA - Cast | 25.6 | 93.05 | 0.66 |

Composite     3DP only     Cast 20% PVA

| | Ultimate tensile strength | | | | Tensile (elastic) modulus | | |
|---|---|---|---|---|---|---|---|
| | Cast PVA | Chitosan/PVA mesh | Composite | | Cast PVA | Chitosan/PVA mesh | Composite |
| Mean | 0.66 | 0.98 | 1.51 | Mean | 0.23 | 0.44 | 0.62 |
| Std. Deviation | 0.082 | 0.099 | 0.195 | Std. Deviation | 0.025 | 0.038 | 0.053 |

BIOPRINTED MENISCUS IMPLANT AND METHODS OF USING SAME

CROSS-REFERENCE TO RELATED APPLICATIONS

The present application is related to U.S. Provisional Appl. No. 62/608,523, filed on Dec. 20, 2018, the contents of which are hereby incorporated by reference in their entirety and for all purposes.

FIELD OF THE INVENTION

The invention provides synthetic tissue structures and methods for their fabrication and use, including artificial meniscus implants, comprising precisely patterned layers of composite hydrogel materials replicating the mechanical properties of endogenous meniscal tissue.

BACKGROUND OF THE INVENTION

The meniscus is one of the most commonly damaged areas of the knee joint, with a mean incidence of injury in the United States of 66 injuries per 100,000 people. Complete or partial removal of the meniscus relieves acute pain, but without adequate replacement, meniscus removal can lead to damage of the articular cartilage of the knee, leading to osteoarthritis (OA). The meniscus typically demonstrates poor healing potential, and none of the currently available meniscal replacement options meets the necessary load-bearing and biomechanical requirements of this unique tissue, while also successfully engrafting into the surrounding tissue to provide a long-term solution to meniscus injury.

In particular, the micro-anatomic geometry of the meniscus is closely associated with its biomechanical properties. The hydrated nature of the meniscus (~72% water) confers resistance to compressive stress, as water is incompressible, however, the meniscus also has considerable tensile strength as well which is conferred via the ordered arrangement of collagen fibers throughout the tissue. Interactions among the important constituents of the fibrocartilage matrix cause meniscal tissue to behave as a fiber-reinforced, porous, permeable composite material, in which frictional drag caused by fluid flow governs its response to dynamic loading. The surface and lamellar zones of the meniscus are made up of randomly oriented collagen fibers, whereas fibers deeper in the meniscus are oriented in circumferential and radial directions. With normal use, forces of several times body weight arise within the knee, with the menisci transmitting 50-100% of this load through the dense network of circumferentially aligned collagen fibers. This ordered architecture engenders very high tensile properties in the fiber direction (tensile modulus 50-300 MPa) (Baker & Mauck, 2007) (Fithian et al., 1990).

Tensile hoop stress is created in the circumferential direction when the knee bears an axial load, and this stress tries to extrude the meniscus out of the knee joint. However, the tensile strength of circumferentially-aligned collagen fibers and the firm attachment at the anterior and posterior insertional ligaments helps prevent extrusion of the meniscus, significantly reduces stress and protects the tibial cartilage. In contrast, if the anterior or posterior insertional ligaments or peripheral circumferential collagen fibers rupture, the load transmission mechanism changes and can damage the tibial cartilage. Compressive strength has been measured in fresh-frozen cadaveric human menisci, the axial and radial unconfined compressive Young's moduli at 12% strain were 83.4 kPa and 76.1 kPa, respectively at equilibrium. When subject to a physiological strain rate relevant to walking, the axial and radial compressive moduli at 12% strain were 718 kPa and 605 kPa respectively (Chia & Hull, 2008), with tensile modulus several orders of magnitude greater (50-300 MPa) (Baker & Mauck, 2007) (Fithian et al., 1990).

Accordingly, naturally-occurring meniscal tissue possesses significant tensile and compressive strength, a remarkable combination that has proven difficult to recreate in synthetic structures. In US 2017/0202672, for example, a molded artificial meniscus is described comprising a shell of polycaprolactone (PCL) and a polycarbonate urethane (PCU) core reinforced with Kevlar fibres. Unfortunately, however, surrounding the reinforced PCU/Kevlar core with a relatively stiff and brittle PCL coat does not even approximate native mechanical characteristics, since the compressive modulus of bulk PCL is orders of magnitude greater than the measured compressive modulus of human meniscus tissue (~300 MPa for PCL v. ~70-1000 kPa for human meniscus dependent on the strain %, rate and orientation). As such, synthetic structures, such as the reinforced PCU/Kevlar core may lead to a high risk of premature implant failure and potential damage to the existing meniscus tissue or surrounding articular cartilage.

Similarly, WO 2015/026299 describes an electrojetting technique employing PCL soluble in volatile organic solvents, creating a meshwork of fibres arranged in concentric and rectilinear patterns but all made from the same material. As noted above, however, PCL alone does not possess appropriate mechanical properties with respect to compressive modulus and viscoelasticity to match the host meniscus, and mismatches in compressive modulus between implant and host meniscus may lead to graft failure and joint damage. Moreover, although PCL can support cell attachment the implant will be populated by cells at different rates in different regions, and thus as the PCL biodegrades the implant will likely fail due to degradation in regions that are not appropriately populated and reinforced by living cells.

As such, conventional approaches and materials used for the construction of artificial meniscus implants have thus far failed to produce structures having the requisite level of tensile and compressive strength, on the one hand, and physiological compatibility and cellular viability on the other. Moreover, the prior art structures and materials also fail to address another critical mechanical characteristic, suture retention strength, which is important to avoid suture pull-out of an implanted meniscus tissue. The current invention addresses these and other unmet needs. All prior art references listed herein are incorporated by reference in their entirety.

SUMMARY OF INVENTION

The present invention is based, in part, on the unexpected observation that certain composite hydrogel materials can be successfully employed in bioprinted meniscal implants to more closely replicate the mechanical characteristics of natural meniscal tissue with regards to both tensile and compressive strength. Critically, the composite materials described herein further provide adequate suture pull-out strength, thereby enabling safe and effective fixation of the resulting meniscal implant within the knee joint. Aspects of the present invention include meniscal tissue structures comprising at least one layer of reinforced composite hydrogel deposited by a bioprinter, and methods of making same, wherein the composite hydrogel can be reinforced simultaneously with, or more preferably, sequentially after printing.

In one aspect, the invention provides a meniscal implant comprising a plurality of layers deposited by a bioprinter, each layer comprising synthetic tissue fiber(s) comprising a solidified biocompatible matrix, wherein the solidified biocompatible matrix in at least one layer of the meniscal implant comprises a reinforced composite hydrogel, and preferably throughout said layer. In some embodiments, one or more synthetic tissue fibers are dispensed in a desired pattern or configuration to form a first layer, and one or more additional layers are then dispensed on top, having a different pattern or configuration.

In an exemplary embodiment, one or more layers of circumferentially-oriented synthetic tissue fiber(s) are alternated with one or more layers of radially-oriented synthetic tissue fiber(s). In some embodiments, the circumferentially-oriented synthetic tissue fiber(s) comprises a first solidified biocompatible matrix, e.g. a reinforced composite hydrogel, and the radially-oriented synthetic tissue fiber(s) comprises a second, different solidified biocompatible matrix, e.g. a softer, cell-compatible hydrogel material, or a second reinforced composite hydrogel. In some embodiments, the circumferentially-oriented synthetic tissue fiber(s) and the radially-oriented synthetic tissue fiber(s) comprise the same solidified biocompatible matrix.

In preferred embodiments, the reinforced composite hydrogel in at least one layer of the meniscal implant comprises a hydrogel material selected from the group consisting of alginate and chitosan, and a reinforcement material selected from the group consisting of polyethylene (glycol) diacrylate (PEGDA), polyethylene (glycol) methacrylate (PEGMA), gelatin methacryloyl (GelMA), polyacrylic acid (PAA), and poly (vinyl alcohol) (PVA), or combinations thereof. In one preferred embodiment, the hydrogel material comprises alginate or chitosan and the reinforcement material comprises an acrylated PEG derivative, e.g. PEGDA. In another preferred embodiment, the hydrogel material comprises chitosan and the reinforcement material comprises PVA. In another preferred embodiment, the hydrogel material comprises chitosan and the reinforcement material comprises both PVA and PEGDA.

In some embodiments, cross-linking of the reinforcement material occurs post-printing. In some embodiments, both addition and cross-linking of the reinforcement material occurs post-printing. In some embodiments, a first reinforcement material is blended with the hydrogel material and cross-linked either simultaneously or sequentially with printing, and a second reinforcement material is added to the printed layers and crosslinked post-printing, e.g. as a cast matrix. In some embodiments, directional pressure is applied to the second reinforcement material by way of, e.g., centrifugation or vacuum, to increase infiltration of the second reinforcement material into the printed layers. In some embodiments, the infill density of the printed layers is less than 90%, 85%, 80%, 75%, 70%, 65%, 60%, 55%, 50%, 45% 40%, 35%, 30%, 25%, 20%, 15% or 10% before addition of the second reinforcement material. In some embodiments, the first and second reinforcement materials are the same. In a particular embodiment, the first and second reinforcement materials are both PVA. In some embodiments, the first and second reinforcement materials are different. In a particular embodiment, the first reinforcement material is PVA and the second reinforcement material is PEGDA.

In exemplary embodiments, the hydrogel material comprises between about 2.5% and 6% (w/v) chitosan, e.g., at least about 2.5% (w/v) chitosan, more preferably at least about 3.0% (w/v) chitosan, more preferably at least about 3.5% (w/v) chitosan, more preferably at least about 4.0% (w/v) chitosan, and still more preferably at least about 4.5% (w/v) chitosan. In some embodiments, the chitosan is cross-linked with a crosslinker comprising sodium tripolyphosphate (STP). In one embodiment, the STP-based crosslinker comprises at least about 1% STP concentration, more preferably at least about 1.5%, still more preferably at least about 2.0%, most preferably at least about 2.5% STP. In some embodiments, the STP-based crosslinker further comprises polyethylene glycol, and preferably a higher molecular weight PEG, e.g., PEG 20000. In one embodiment the STP-based crosslinker comprises between about 10-20% PEG20000, more preferably between about 12-18% PEG20000, most preferably about 15% PEG20000.

In further embodiments, the reinforced composite hydrogel comprises a blend of chitosan and PVA, and preferably in a 1:1 ratio (w/w). In some embodiments, the hydrogel material comprises at least about 2.5%, 3.0%, 3.5%, 4.0%, or 4.5% (w/v) chitosan blended in a 1:1 ratio with a reinforcement materials comprising at least about 10%, 11%, 12%, 13%, 14%, 15%, 16%, 17%, 18%, 19% or 20% PVA, more preferably between about 13% and 17% PVA, and most preferably about 15% PVA.

In exemplary embodiments, the reinforced composite hydrogel comprises alginate or chitosan and a PEGDA having a molecular weight between about 1000 and 6000 Da, more preferably between about 1000 and 4000 Da, most preferably about 3400 Da. In some embodiments, the PEGDA is crosslinked with a photoinitiator (e.g., Irgacure 2959) and UV light. In some embodiments, the PEGDA is crosslinked via free radical release (e.g. with ammonium persulfate (APS) and tetramethylethylenediamine (TEMED). In preferred embodiments, both the addition and cross-linking of PEGDA occur post-printing as a second reinforcement material.

In some embodiments, an artificial meniscus implant has an arcuate shape that has an anterior end, a posterior end, a middle section therebetween defining a curved path between said anterior and posterior ends, an internal side, and an external side.

In another aspect, methods of making a meniscal implant are provided, comprising depositing synthetic tissue fiber(s) from a bioprinter to form a plurality of layers, each layer comprising a solidified biocompatible matrix, wherein the solidified biocompatible matrix in at least one layer of the meniscal implant comprises a reinforced composite hydrogel, and preferably throughout said layer. In some embodiments, one or more synthetic tissue fibers are dispensed in a desired pattern or configuration to form a first layer, and one or more additional layers are then dispensed on top, having a different pattern or configuration.

In an exemplary embodiment, one or more layers of circumferentially-oriented synthetic tissue fiber(s) are alternated with one or more layers of radially-oriented synthetic tissue fiber(s). In some embodiments, the circumferentially-oriented synthetic tissue fiber(s) comprises a first solidified biocompatible matrix, e.g. a reinforced composite hydrogel, and the radially-oriented synthetic tissue fiber(s) comprises a second, different solidified biocompatible matrix, e.g. a softer, cell-compatible hydrogel material, or a second reinforced composite hydrogel. In some embodiments, the circumferentially-oriented synthetic tissue fiber(s) and the radially-oriented synthetic tissue fiber(s) comprise the same solidified biocompatible matrix.

In preferred embodiments, the reinforced composite hydrogel in at least one layer of the meniscal implant comprises a hydrogel material selected from the group consisting of alginate and chitosan, and a reinforcement material selected from the group consisting of polyethylene (glycol) diacrylate (PEGDA), polyethylene (glycol) methacrylate (PEGMA), gelatin methacryloyl (GelMA), polyacrylic acid (PAA), and poly (vinyl alcohol) (PVA), or combinations thereof. In one preferred embodiment, the hydrogel material comprises alginate or chitosan and the reinforcement material comprises an acrylated PEG derivative, e.g. PEGDA. In another preferred embodiment, the hydrogel material comprises chitosan and the reinforcement material comprises PVA. In another preferred embodiment, the hydrogel material comprises chitosan and the reinforcement material comprises both PVA and PEGDA.

In some embodiments, the method further comprises cross-linking of the reinforcement material after printing of the layers. In some embodiments, the method further comprises addition and crosslinking of the reinforcement material after printing of the layers. In preferred embodiments, the method further comprises blending a first reinforcement material with the hydrogel material before printing, and cross-linking said first reinforcement after printing. In particularly preferred embodiments, the method further comprises adding a second reinforcement material to the layers after printing, and crosslinking the resulting structure, e.g. as a cast matrix. In some embodiments, the method further comprises applying directional pressure to the second reinforcement material by way of, e.g., centrifugation or vacuum, to increase infiltration of the second reinforcement material into the printed layers. In some embodiments, the infill density of the printed layers is less than 90%, 85%, 80%, 75%, 70%, 65%, 60%, 55%, 50%, 45% 40%, 35%, 30%, 25%, 20%, 15% or 10% before addition of the second reinforcement material. In some embodiments, the first and second reinforcement materials are the same. In a particular embodiment, the first and second reinforcement materials are both PVA. In some embodiments, the first and second reinforcement materials are different. In a particular embodiment, the first reinforcement material is PVA and the second reinforcement material is PEGDA.

In exemplary embodiments, the hydrogel material comprises between about 2.5% and 6% (w/v) chitosan, e.g., at least about 2.5% (w/v) chitosan, more preferably at least about 3.0% (w/v) chitosan, more preferably at least about 3.5% (w/v) chitosan, more preferably at least about 4.0% (w/v) chitosan, and still more preferably at least about 4.5% (w/v) chitosan. In some embodiments, the chitosan is cross-linked with a crosslinker comprising sodium tripolyphosphate (STP). In one embodiment, the STP-based crosslinker comprises at least about 1% STP concentration, more preferably at least about 1.5%, still more preferably at least about 2.0%, most preferably at least about 2.5% STP. In some embodiments, the STP-based crosslinker further comprises polyethylene glycol, and preferably a higher molecular weight PEG, e.g., PEG 20000. In one embodiment the STP-based crosslinker comprises between about 10-20% PEG20000, more preferably between about 12-18% PEG20000, most preferably about 15% PEG20000.

In further embodiments, the reinforced composite hydrogel comprises chitosan and PVA in a 1:2, 2:1 or 1:1 ratio, and preferably in a 1:1 ratio (w/w). In some embodiments, the hydrogel material comprises at least about 2.5%, 3.0%, 3.5%, 4.0%, or 4.5% (w/v) chitosan blended in a 1:1 ratio with a reinforcement material comprising at least about 10%, 11%, 12%, 13%, 14%, 15%, 16%, 17%, 18%, 19% or 20% PVA, more preferably between about 13% and 17% PVA, and most preferably about 15% PVA.

In exemplary embodiments, the reinforced composite hydrogel comprises alginate or chitosan and a PEGDA having a molecular weight between about 1000 and 6000 Da, more preferably between about 1000 and 4000 Da, most preferably about 3400 Da. In some embodiments, the PEGDA is crosslinked with a photoinitiator (e.g., Irgacure 2959) and UV light. In some embodiments, the PEGDA is crosslinked via free radical release (e.g. with ammonium persulfate (APS) and tetramethylethylenediamine (TEMED). In preferred embodiments, both the addition and cross-linking of PEGDA occur post-printing as a second reinforcement material.

BRIEF DESCRIPTION OF THE DRAWINGS

FIG. 12 shows a direct comparison of printed, cast, and composite chitosan:PVA tissues. Tissues were fabricated using printed fibers of 4.5% LMW chitosan+15% 146-186 k PVA, 1:1 by weight. Chitosan:PVA fibers printed at 12% in-fill density were tested either with or without a secondary matrix of 20% 146-186 k PVA. A third group of cast 20% PVA-only tissues were also tested. All tissues were exposed to several freeze-thaw cycles to crystallize and harden the PVA.

DETAILED DESCRIPTION

Figure 1:
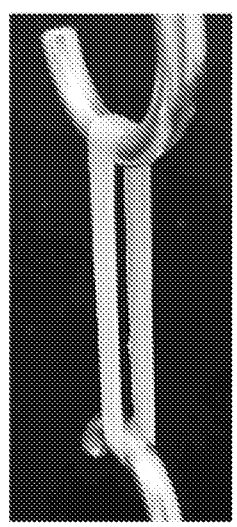
FIG. 1 is a graph showing the effect of the molecular weight (Mw) of polyethylene glycol diacrylate (PEGDA) on the mechanical properties of printed alginate:PEGDA rings. 200 ul of each PEGDA solution with the photoinitiator Irgacure® 2959 (as indicated) was added after printing alginate rings ("LVM"=high strength, very soft and stretchy alginate). PEGDA was cross-linked after addition to printed alginate rings via UV exposure causing free radical release. As seen in the graph, different Mws give different polymer characteristics (low Mw=brittle, high Mw=softer and stretchy) and some result in a steeper curve and the steeper the curve, the stiffer the material is (higher modulus).
Figure 1:
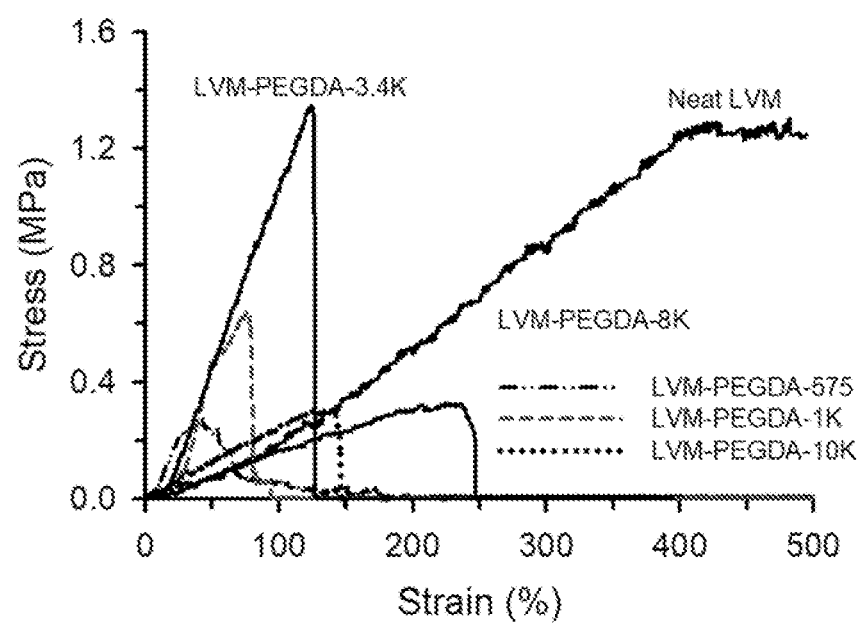

Aspects of the present invention include synthetic tissue structures comprising a plurality of layers deposited by a bioprinter, each layer comprising synthetic tissue fiber(s) comprising a solidified biocompatible matrix, wherein the solidified biocompatible matrix in at least one layer of the tissue structure comprises a reinforced composite hydrogel, and preferably throughout said layer. The term "solidified" as used herein refers to a solid or semi-solid state of material that maintains its shape fidelity and structural integrity upon deposition. The term "shape fidelity" as used herein means the ability of a material to maintain its three dimensional shape. In some embodiments, a solidified material is one having the ability to maintain its three dimensional shape for a period of time of about 30 seconds or more, such as about 1, 10 or 30 minutes or more, such as about 1, 10, 24, or 48 hours or more. The term "structural integrity" as used herein means the ability of a material to hold together under a load, including its own weight, while resisting breakage or bending.

In some embodiments, a solidified composition is one having a Young's (elastic) modulus under unconfined compression at 12% strain at equilibrium, greater than about 15, 20 or 25 kilopascals (kPa), more preferably greater than about 30, 40, 50, 60, 70, 80 or 90 kPa, still more preferably greater than about 100, 110, 120 or 130 kPa with a maximum compressive elastic modulus of 1,000 kPa, more preferably less than about 900, 800, 700, 600 or 500 kPa. Preferred unconfined compressive elastic modulus ranges at 12% strain level at physiological strain rates representing activities such as walking should preferably be greater than 200 kPa to a maximum of about 2,000 kPa.

In some embodiments a solidified composition is one having a Young's modulus under tension of greater than about 1, 2, or 3 megapascals (MPa), more preferably greater than about 5, 10, 15, or 20 MPa, still more preferably greater than 25 or 30 MPa, up to a maximum ideal tensile modulus of less than 2000 MPa, ideally less than 1,800, 1,600, 1,400 or 1,200 MPa, still more ideally less than 1,000, 900, 800, 700, 600 and 500 MPa.

Additional aspects of the invention include artificial meniscus implants for use in repairing and/or replacing a damaged or diseased meniscal tissue in a mammalian subject, comprising synthetic tissue fiber(s) dispensed from a bioprinter as a solidified biocompatible matrix, wherein the solidified biocompatible matrix comprises a reinforced composite hydrogel.

The solidified biocompatible matrix may advantageously comprise alginate or chitosan as hydrogel material, or any other suitable biocompatible polymer that can be instantaneously solidified while dispensing from the printhead. In a preferred embodiment, the alginate-based matrix is printed and simultaneously crosslinked at the time of printing by contacting with a divalent cation crosslinking solution (e.g., a $CaCl_2$) solution) before or upon dispensation from the printhead. In another preferred embodiment, the chitosan-based matrix is printed and simultaneously crosslinked at the time of printing by contacting with a multivalent anion crosslinking solution (e.g. a sodium tripolyphosphate ($Na_5P_3O_{10}$) solution) before or upon dispensation from the printhead. In particularly preferred embodiments, the alginate or chitosan biocompatible matrix further comprises one or more reinforcement materials, as described in more detail herein. In further preferred embodiments, the solidified biocompatible matrix comprises a homogeneous composition of alginate or chitosan throughout the radial cross section of each synthetic tissue fiber.

In some embodiments, one or more synthetic tissue fibers are dispensed in a desired pattern or configuration to form a first layer, and one or more additional layers are then dispensed on top, having the same or a different pattern or configuration. In certain embodiments, a plurality of layers are stacked to form a three dimensional structure that can be used as an artificial meniscus implant. Preferably, at least one of said layers comprises a single continuous synthetic tissue fiber dispensed from the bioprinter having a variable composition. More preferably, each of said layers comprises a single continuous synthetic tissue fiber having a variable composition.

In some embodiments, a synthetic tissue structure comprises a number of individual layers that ranges from about 1 to about 250, such as about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 200, 205, 210, 215, 220, 225, 230, 235, 240 or about 245 individual layers. Any suitable number of individual layers can be incorporated to generate a tissue structure having desired dimensions.

In some embodiments, one or more individual fibers and/or layers are organized to create one or more zones within a tissue structure, wherein each zone has one or more desired properties (e.g., one or more mechanical and/or biological properties). As used herein, the term "region" refers to a portion of a tissue structure defined in an x-y plane (e.g., an area or portion of an individual layer, where each layer of the tissue structure defines an x-y plane), whereas the term "zone" refers to a portion of a tissue structure defined in the z-direction and comprising at least two contiguous regions from separate x-y planes, or layers (e.g., a "macrolayer" that comprises a plurality of individual "microlayers").

Zones in accordance with embodiments of the invention can have any desired three dimensional geometry, and can occupy any desired portion of a synthetic tissue structure. For example, in some embodiments, a zone can span an entire length, width, or height of a synthetic tissue structure. In some embodiments, a zone spans only a portion of a length, width, or height of a synthetic tissue structure. In some embodiments, a synthetic tissue structure comprises a plurality of different zones that are organized along a length, width, height, or a combination thereof, of the synthetic tissue structure. In one preferred embodiment, a synthetic tissue structure comprises three different zones that are organized along the height of the synthetic tissue structure, such that a path through the synthetic tissue structure from the bottom to the top would pass through all three zones.

In some embodiments, a zone can comprise a number of layers that ranges from about 2 to about 250, such as about 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 200, 205, 210, 215, 220, 225, 230, 235, 240 or about 245 individual layers. In some embodiments, the individual layers within a zone are organized in a manner that confers one or more mechanical and/or biological properties on the zone. For example, in some embodiments, the individual layers within a zone comprise one or more reinforcing materials that confer increased mechanical strength on the zone. In some embodiments, the individual layers within a zone comprise one or more materials that confer desirable cell growth properties on the zone. In some embodiments, the individual layers within a zone, or the plurality of individual compartments of a fiber structure passing through the zone, can be alternated in a manner that confers desirable properties on the zone. For example, in some embodiments, the individual layers or regions within a zone are alternated such that the odd numbered layers contain one or more reinforcing materials that confer desirable mechanical properties on the zone, and the even numbered layers contain one or more materials that confer desirable biological properties on the zone (e.g., softer materials that are conducive to cell migration, growth, viability, and the like). In some embodiments, a zone comprises a plurality of contiguous individual layers (e.g., about 2, 3, 4, 5, 6, 7, 8, 9 or about 10 or more contiguous layers) that comprise one or more reinforcing materials that confer increased mechanical strength on the zone, which contiguous layers are alternated with another plurality of contiguous individual layers (e.g., about 2, 3, 4, 5, 6, 7, 8, 9 or about 10 or more contiguous layers) that comprise one or more materials that confer desirable biological properties on the zone (e.g., softer materials that are conducive to cell migration, growth, viability, and the like).

Synthetic tissue fiber structures in accordance with embodiments of the invention can include controlled patterning of different matrix materials (e.g., natural and/or synthetic polymers) and crosslinking techniques to create a desired cross-sectional profile within a given compartment. For example, in some embodiments, a synthetic tissue fiber structure comprises a compartment having a solid, tubular, or porous cross-sectional profile. Non-limiting examples of cross-sectional profiles that can be created in a synthetic tissue fiber structure in accordance with embodiments of the invention include those described in Jun, Yesl, et al. "Microfluidic spinning of micro- and nano-scale fibers for tissue engineering." *Lab on a Chip* 14.13 (2014): 2145-2160, the disclosure of which is incorporated herein by reference in its entirety.

In some embodiments, the resulting synthetic tissue fiber is patterned, using software tools, to form layers optionally containing a plurality of biocompatible matrix materials. In certain embodiments, a plurality of layers is deposited in a sequential manner to generate a multi-layered meniscus implant comprising a plurality of zones. In some embodiments, a meniscus implant comprises at least one basal zone, at least one interior zone, and at least one superficial zone, wherein the interior zone comprises at least one layer comprising at least one circumferentially-oriented synthetic tissue fiber, and at least one radially-oriented synthetic tissue fiber. Preferably, at least one of said layers comprises a single continuous synthetic tissue fiber dispensed from the bioprinter comprising a reinforced composite hydrogel.

One advantage of the subject meniscus implants is that the matrix composition can be controlled at any given point in any portion of any layer of the implant, thereby facilitating the generation of meniscus implants more closely resembling the natural architecture of a meniscus tissue, and that possess desirable biomechanical properties, including, but not limited to, reinforced anchor regions on the periphery of the implant, and circumferentially- and radially-oriented fiber structures within the meniscus implant.

In certain embodiments, the subject meniscus implants are generated using automated control systems that modulate one or more characteristics of the synthetic tissue fiber(s) to achieve, e.g., material switching within an individual fiber structure, between separate fiber structures, within or across a layer, within or across a zone, and essentially at any point throughout the structure. As a result, point to point control of the meniscus implant composition is achieved. Furthermore, key parameters, such as fiber diameter and layer thickness, can also be modulated as desired. This level of automated control is essential to accurately recreating the heterogeneous composition and morphology found in native knee menisci.

Biocompatible Matrix Materials:

The solidified biocompatible matrix may comprise any of a wide variety of natural or synthetic polymers that support the viability of living cells, including, e.g., alginate, laminin, fibrin, hyaluronic acid, poly(ethylene) glycol based gels, gelatin, chitosan, agarose, or combinations thereof. In preferred embodiments, the solidified biocompatible matrix comprises alginate or chitosan, or other suitable biocompatible polymers that can be instantaneously solidified while dispensing from the printhead.

Aspects of the invention include single network hydrogels and composite hydrogels. Single network hydrogels are composed of a single hydrogel material, such as alginate, chitosan or PEGDA, for example and large amounts of water (50-90%). Depending on the material, the crosslinked hydrogel network can be generated by various mechanisms, such as covalent, ionic or physical crosslinking which includes hydrogen bonding and hydrophobic interactions. A blended hydrogel material can be composed of two or more materials that are combined generally before crosslinking in liquid state. A network comprising these different materials is then generated by crosslinking the different components either simultaneously or sequentially through appropriate methods. In this combined network, the different hydrogels can form an interpenetrating network (IPN) or a semi-IPN in which the different networks are entangled and co-exist in the same space. Otherwise, the materials can be separated into different microscopic areas. A composite hydrogel can also comprise the same material in different forms, such as the same polymer in different molecular weights, which can also generate a network with different properties than a single network hydrogel. Double network hydrogels (DNH), or in some cases triple or even quadruple network hydrogels, are interpenetrating hydrogel networks created by simultaneous or sequential crosslinking of materials with contrasting properties, such as a rigid, brittle material and a soft, ductile material. As demonstrated herein, with the right combination of materials double network hydrogels can have dramatically enhanced mechanical properties, such as high strength and toughness. This great enhancement in mechanical properties is what is considered to separate true DNHs from other IPN or semi-IPN hydrogels. Thus the distinction between DNH and other multicomponent hydrogels is based on mechanical performance of the composite hydrogel material compared to the individual components.

In some embodiments, the composite hydrogel comprises a blend of alginate or chitosan and polyethylene glycol diacrylate (PEGDa). In one embodiment, the blend comprises an alginate solution having a concentration ranging from 1-8% (w/v) in water, such as 2-6%, and a PEGDa solution having a concentration that ranges from 50-100% (w/v) in water. In some embodiments, the PEGDa has an average molecular weight that ranges from 1 kDa to 6 kDa, more preferably 1-4 kDa, most preferably 3.4 kDa. A non-limiting example of a preparation process for a PEGDa solution is as follows: liquid PEGDa or solid powder is dissolved in water by magnetic stirring at room temperature. Photoinitiator ("PI"), 2-Hydroxy-4'-(2-hydroxyethoxy)-2-methylpropiophenone (Irgacure 2959) is dissolved in the PEGDa solution at a concentration that ranges from 0.1-1.0% by magnetic stirring.

A non-limiting example of a preparation process for an alginate/PEGDa blend is as follows: alginate and PEGDa solutions containing photoinitiator are mixed by magnetic stirring at different concentrations of PEGDa with respect to alginate (concentration of PEGDa varied from 50-100%). A composite solution is prepared fresh before printing to avoid photodecomposition of PEGDa and photoinitiator.

A crosslinker solution can comprise 50-125 mM Calcium Chloride in 1-5% PVA solution in water. In one particular embodiment, a crosslinker solution comprises 125 mM $CaCl_2$) in 2% PVA solution. Printing of the implants is accomplished by ionically crosslinking alginate with $Ca^{2+}$ during printing to create alginate fibers while PEGDa remained uncrosslinked and embedded into the alginate fibers. After printing, crosslinking of PEGDa is attained by irradiating with 365 nm UV light for 5-40 min resulting in second network.

In preferred embodiments, the composite hydrogel comprises a double network hydrogel of alginate or chitosan and polyethylene glycol diacrylate (PEGDa) prepared by impregnation of PEGDa into printed constructs. In one embodiment, a hydrogel comprises an alginate solution having a concentration ranging from 1-8% (w/v) in water, such as 2-6%. A crosslinker solution can comprise 50-125 mM Calcium Chloride in 1-5% PVA solution in water. In one particular embodiment, a crosslinker solution comprises 125 mM $CaCl_2$) in 2% PVA solution.

A PEGDa solution having a concentration that ranges from 50-100% (w/v) in water is used. In some embodiments, the PEGDa has an average molecular weight that ranges from 1 kDa to 6 kDa, more preferably from 1 kDa to 4 kDa, and most preferably 3.4 kDa. A non-limiting example of a preparation process for a PEGDa solution is as follows: liquid PEGDa or solid powder is dissolved in water by magnetic stirring at room temperature. Photoinitiator, 2-Hydroxy-4'-(2-hydroxyethoxy)-2-methylpropiophenone (Irgacure 2959) is dissolved in the PEGDa solution at a concentration that ranges from 0.1-1.0% by magnetic stirring. Optionally, a composition can include CNC in the PEGDa/photoinitiator solution. In some embodiments, the concentration of CNC can range from 5-50% of the weight of PEGDa.

A non-limiting example of a preparation process for a double network hydrogel is as follows: PEGDa solutions containing photoinitiator are poured onto printed constructs drop by drop and allowed to soak in the dark overnight at room temperature. In some embodiments, the concentration of PEGDa is varied from 50-100%. After overnight soaking, crosslinking of PEGDa in the printed constructs is accomplished by irradiating with 365 nm UV light for 5-40 min resulting in second network. Alternatively, and advantageously, the PEGDA may also be crosslinked with ammonium persulfate (APS) and tetramethylethylenediamine (TEMED) via direct free radical release. In preferred embodiments, the addition and cross-linking of PEGDA occurs post-printing as a second reinforcement material.

In some embodiments, an implant comprises chitosan-polyvinyl alcohol (PVA) blends comprising the following:

Chitosan solution: 1-10% (w/v) in 2% acetic acid, preferably between about 2.5% and 6% (w/v) chitosan, e.g., at least about 2.5% (w/v) chitosan, more preferably at least about 3.0% (w/v) chitosan, more preferably at least about 3.5% (w/v) chitosan, more preferably at least about 4.0% (w/v) chitosan, and still more preferably at least about 4.5% (w/v) chitosan.

PVA solution: 10-40% (such as 10-20%) in a 1:1 (w/v) ratio with the chitosan, preferably at least about 10%, 11%, 12%, 13%, 14%, 15%, 16%, 17%, 18%, 19% or 20% PVA, more preferably between about 13% and 17% PVA, and most preferably about 15% PVA in water or in a salt solution, prepared by autoclaving for 15 min in 121° C.

Blend preparation: Chitosan and PVA solutions combined in different ratios and vortexed and mixed with a magnetic stirrer. Ratios of Chitosan:PVA 2:1, 1:1, 1:2, for example. Blends prepared fresh for each print to avoid the effect of PVA aging on printability (PVA solutions become more viscous over time in RT).

Crosslinker solution: 1-10% sodium tripolyphosphate (STP) in 1-20% polyethylene glycol (PEG, Mw=20000). In one particular embodiment, 2.5% STP in 15% PEG20k Printing: Chitosan ionically crosslinked with STP during printing to create chitosan-PVA fibers. PVA gelled post-printing using freeze-thaw cycling and/or salt soak (brine or sodium sulfate). Chitosan-PVA blends and core-shell fibers with a chitosan-PVA shell and a pure PVA core printed and tested.

In some embodiments, the chitosan is cross-linked with a crosslinker comprising sodium tripolyphosphate (STP). In one embodiment, the STP-based crosslinker comprises at least about 1% STP concentration, more preferably at least about 1.5%, still more preferably at least about 2.0%, most preferably at least about 2.5% STP. In some embodiments, the STP-based crosslinker further comprises polyethylene glycol, and preferably a higher molecular weight PEG, e.g., PEG 20000. In one embodiment the STP-based crosslinker comprises between about 10-20% PEG20000, more preferably between about 12-18% PEG20000, most preferably about 15% PEG20000.

In some embodiments, an implant optionally comprises a blend of alginate and cellulose nanocrystals (CNCs). In some embodiments, a blend comprises an alginate solution having a concentration ranging from 1-8% (w/v) in water, such as 2-6%, and a CNC dispersion having a concentration that ranges from 1-6% (w/v) in water. A non-limiting example of a preparation process for a CNC dispersion is as follows: a blend is prepared by acid-hydrolysis of fully-bleached commercial kraft softwood pulp with 64 wt % sulfuric acid (8.75 mL of a sulfuric acid solution per gram of pulp) at 45° C. with vigorous stirring for 25 min. Surface modification of CNC can be performed, e.g., by TEMPO-mediated oxidation.

A non-limiting example of a preparation process for an alginate/CNC blend is as follows: an alginate solution is prepared by magnetic stirring at room temperature; a CNC dispersion is prepared by magnetic stirring and ultrasonication at room temperature; and composite solutions (i.e., blends) of alginate and CNC are prepared by mixing with magnetic stirring at different concentrations of CNC with respect to alginate. In some embodiments, the concentration of CNCs is varied from 5-50%. Composite dispersions can be prepared fresh before printing to avoid precipitation and inhomogeneity of concentration of CNCs.

A crosslinker solution can comprise 50-125 mM Calcium Chloride in 1-5% PVA solution in water. In one particular embodiment, a crosslinker solution comprises 125 mM $CaCl_2$) in 2% PVA solution. Printing of the implants is accomplished by ionically crosslinking alginate with $Ca^{2+}$ during printing to create alginate fibers. TEMPO-modified CNCs possess surface carboxyl groups that help them become homogeneously dispersed in the alginate solution and crosslinked via $Ca^2$ ions resulting in alginate-CNC composite fibers.

In some embodiments, the solidified biocompatible matrix is physiologically compatible, i.e., conducive to cell growth, differentiation and communication. By "physiological matrix material" is meant a biological material found in a native mammalian tissue. Non-limiting examples of such physiological matrix materials include: fibronectin, thrombospondin, glycosaminoglycans (GAG) (e.g., hyaluronic acid, chondroitin-6-sulfate, dermatan sulfate, chondroitin-4-sulfate, or keratin sulfate), deoxyribonucleic acid (DNA), adhesion glycoproteins, and collagen (e.g., collagen I, collagen II, collagen III, collagen IV, collagen V, collagen VI, or collagen XVIII).

In some embodiments, higher strength fibers may also be generated from high concentrations of biological polymers, including, but not limited to: collagen, chitosan, silk fibroin, or any combination thereof, and these may be incorporated into one or more anchor regions.

In some embodiments, high strength fibers can be incorporated (e.g., patterned) into one or more reinforced peripheral regions of an artificial meniscus implant to increase strength along the periphery of the implant. In some embodiments, high strength fibers are incorporated into the entire periphery of the implant. Within an anchor region and/or a reinforced peripheral region of an artificial meniscus implant, layers of high strength material can be alternated with layers of softer material that is optimized for cell survival and ingrowth. Increased strength within anchor regions and/or reinforced peripheral region can be conferred by increasing the concentration of a fiber material, by increasing the infill density of the printed fibers, by increasing the diameter of the printed fibers, or by any combination thereof. In some embodiments, an anchor region can be colored by incorporating, e.g., a non-toxic dye into the printable anchor material to act as a visual guide during surgery, thereby informing the surgeon of the location of the reinforced areas of the artificial meniscus implant that are adapted for placement of sutures.

In the human meniscus, the correct orientation and alignment of collagen fibers is crucial to confer appropriate biomechanical properties to the tissue. In certain embodiments, therefore, the subject meniscus implants further comprise a layer wherein one or more synthetic tissue fiber structures are configured to promote alignment of microfibers of the synthetic polymer chains or biological matrix such as collagen fibrils parallel to the longitudinal direction of the synthetic tissue fiber. As such, in certain embodiments, a synthetic tissue fiber(s) is deposited in a radial and/or a circumferential orientation, and is configured to promote alignment of synthetic polymer microfibers, and biological collagen fibers along the radial and/or circumferential directional orientation of the synthetic tissue fiber(s). In this way, circumferential and/or radial orientation of strengthening polymer fibers and collagen fibers can be achieved.

In some embodiments, the diameter of a synthetic tissue fiber is modulated between about 20 μm and about 500 μm to modulate the longitudinal arrangement of polymer chains and/or collagen fibrils within the printed fibers to confer appropriate orientation in different regions of the tissue; e.g. larger diameter fibers at the surface and periphery of the meniscus will contain randomly-oriented (e.g., disordered) polymer chains and collagen fibrils, whereas smaller diameter fibers in the inner region(s) will contain longitudinally-aligned polymer chains and collagen fibrils, resulting in the circumferential and radial patterning of microscopic fibrils to match the orientation of the printed fibers.

Meniscus Injury and Options for Surgical Repair

Damage to the meniscus is very common in the knee joint. Meniscal lesions are typically categorized by distinct age groups. Meniscal injuries in younger human patients (<40 years) are usually caused by trauma or congenital meniscal diseases, whereas those in older human patients (>40 years) tend to be associated with degenerative tears. Meniscal injuries can simply be classified clinically into peripheral meniscal lesions and avascular meniscal lesions. Numerous surgical techniques have been developed to repair meniscal tears in the vascular (red-red) zone with high overall success rates in young patients with stable knees (63-91%). Damage and tearing in the avascular (white-white) zone of the meniscus are often associated with a poor prognosis following repair and consequently several different therapeutic strategies have been attempted with varied results. The most notable include the use of parameniscal synovial tissue, trephination of the peripheral meniscus rim with suture of the meniscus tear, creation of vascular access channels, and the use of mesenchymal stem cells and/or growth factors. None of the above techniques have been generally adopted, thus the main strategy of orthopedic surgeons is to perform a partial meniscectomy in cases of unrepairable or degenerative meniscal injuries, even though this treatment strategy does not prevent the development of knee OA. A partial meniscectomy can result in OA by decreasing the contact area between the femoral condyle and tibial platform. Altering the loading characteristics of the articular knee cartilage can lead to progressive degeneration of meniscus and articular cartilage via a vicious cycle of damage, inflammation and further tissue degeneration.

Artificial Meniscus Implants:

As reviewed above, aspects of the invention include artificial meniscus implants comprising a plurality of layers deposited by a bioprinter, each layer comprising synthetic tissue fiber(s) comprising a solidified biocompatible matrix, wherein the solidified biocompatible matrix in at least one layer of the tissue structure comprises a reinforced composite hydrogel. In some embodiments, at least one layer of the subject artificial meniscus implant can comprise at least one circumferentially and/or radially oriented synthetic tissue fiber. The circumferential and/or radial fiber(s) can have the same or different diameters, and/or the same or different matrix materials.

In certain embodiments, a synthetic tissue fiber is configured to promote deposition of collagen fibers and synthetic polymer chains aligned with the longitudinal direction of the synthetic tissue fiber. In certain embodiments, a synthetic tissue fiber is configured to promote deposition of randomly-oriented collagen or synthetic polymer fibers. In certain embodiments, a subject meniscus implant is constructed using sequential deposition of layers, as described above, such that the meniscus implant comprises an inner, central and outer zone. In certain embodiments, the matrix material present in any given zone can be controlled, thereby creating a meniscus implant that resembles the native architecture and biomechanical characteristics of natural meniscus tissue.

Also provided herein are methods of making a meniscal implant comprising depositing synthetic tissue fiber(s) from a bioprinter to form a plurality of layers, each layer comprising a solidified biocompatible matrix, wherein the solidified biocompatible matrix in at least one layer of the meniscal implant comprises a reinforced composite hydrogel, and preferably throughout said layer. In some embodiments, one or more synthetic tissue fibers are dispensed in a desired pattern or configuration to form a first layer, and one or more additional layers are then dispensed on top, having a different pattern or configuration, e.g., one or more layers of circumferentially-oriented synthetic tissue fiber(s) are alternated with one or more layers of radially-oriented synthetic tissue fiber(s).

In preferred embodiments, the reinforced composite hydrogel in at least one layer of the meniscal implant comprises a hydrogel material selected from the group consisting of alginate and chitosan, and a reinforcement material selected from the group consisting of polyethylene (glycol) diacrylate (PEGDA), polyethylene (glycol) methacrylate (PEGMA), gelatin methacryloyl (GelMA), polyacrylic acid (PAA), and poly (vinyl alcohol) (PVA), or combinations thereof. In one preferred embodiment, the hydrogel material comprises alginate or chitosan and the reinforcement material comprises an acrylated PEG derivative, e.g. PEGDA. In another preferred embodiment, the hydrogel material comprises chitosan and the reinforcement material comprises PVA. In another preferred embodiment, the hydrogel material comprises chitosan and the reinforcement material comprises both PVA and PEGDA.

In some embodiments, the method further comprises cross-linking of the reinforcement material after printing of the layers. In some embodiments, the method further comprises both addition and crosslinking of the reinforcement material after printing of the layers. In preferred embodiments, the method further comprises blending a first reinforcement material with the hydrogel material before printing, and cross-linking said first reinforcement after printing. In particularly preferred embodiments, the method further comprises adding a second reinforcement material to the layers after printing, and crosslinking the resulting structure as a cast matrix.

In some embodiments, the method further comprises applying directional pressure to the second reinforcement material by way of, e.g., centrifugation or vacuum, to increase infiltration of the second reinforcement material into the printed layers before crosslinking. In some embodiments, the infill density of the printed layers is less than 90%, 85%, 80%, 75%, 70%, 65%, 60%, 55%, 50%, 45% 40%, 35%, 30%, 25%, 20%, 15% or 10% before addition of the second reinforcement material. In some embodiments, the first and second reinforcement materials are the same. In a particular embodiment, the first and second reinforcement materials are both PVA. In some embodiments, the first and second reinforcement materials are different. In a particular embodiment, the first reinforcement material is PVA and the second reinforcement material is PEGDA.

In exemplary embodiments, the hydrogel material comprises between about 2.5% and 6% (w/v) chitosan, e.g., at least about 2.5% (w/v) chitosan, more preferably at least about 3.0% (w/v) chitosan, more preferably at least about 3.5% (w/v) chitosan, more preferably at least about 4.0% (w/v) chitosan, and still more preferably at least about 4.5% (w/v) chitosan. In some embodiments, the chitosan is cross-linked with a crosslinker comprising sodium tripolyphosphate (STP). In one embodiment, the STP-based crosslinker comprises at least about 1% STP concentration, more preferably at least about 1.5%, still more preferably at least about 2.0%, most preferably at least about 2.5% STP. In some embodiments, the STP-based crosslinker further comprises polyethylene glycol, and preferably a higher molecular weight PEG, e.g., PEG 20000. In one embodiment the STP-based crosslinker comprises between about 10-20% PEG20000, more preferably between about 12-18% PEG20000, most preferably about 15% PEG20000.

In further embodiments, the reinforced composite hydrogel comprises chitosan and PVA, and preferably in a 1:1 ratio (w/w). In some embodiments, the hydrogel material comprises at least about 2.5%, 3.0%, 3.5%, 4.0%, or 4.5% (w/v) chitosan blended in a 1:1 ratio with a reinforcement material comprising at least about 10%, 11%, 12%, 13%, 14%, 15%, 16%, 17%, 18%, 19% or 20% PVA, more preferably between about 13% and 17% PVA, and most preferably about 15% PVA.

In exemplary embodiments, the reinforced composite hydrogel comprises alginate or chitosan and a PEGDA having a molecular weight between about 1000 and 6000 Da, more preferably between about 1000 and 4000 Da, most preferably about 3400 Da. In some embodiments, the PEGDA is crosslinked with a photoinitiator (e.g., Irgacure 2959) and UV light. In some embodiments, the PEGDA is crosslinked via free radical release (e.g. with ammonium persulfate (APS) and tetramethylethylenediamine (TEMED). In preferred embodiments, both the addition and cross-linking of PEGDA occur post-printing as a second reinforcement material.

Methods for Repairing a Meniscal Defect:

Aspects of the invention include methods for repairing and/or replacing at least a portion of a meniscus in a subject. Any of the meniscus implants described herein can be implanted into a subject in need thereof in order to accomplish meniscus repair or regeneration. Accordingly, methods of repairing a meniscal defect or promoting meniscal regeneration in a subject are also provided herein. In one embodiment, a method comprises implanting a meniscus implant as described herein into a defect site in need of meniscus repair or regeneration.

The term "subject" includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are included. In one embodiment, the subject is a mammal. In one embodiment, the subject is a human subject.

In some embodiments, a method can comprise securing a meniscus implant, or an anchor region thereof, at a defect site, and/or securing one or more anchor regions of a meniscus implant to at least one anatomical structure within a subject. In some embodiments, a method can further comprise removing at least a portion of a defective meniscus from the subject.

All patents and patent publications referred to herein are hereby incorporated by reference in their entirety. Certain modifications and improvements will occur to those skilled in the art upon a reading of the foregoing description. It should be understood that not all such modifications and improvements have been included herein for the sake of conciseness and readability, but are properly within the scope of the following claims.

EXAMPLES

Example 1: Printing with Alginate-Cellulose Nanocrystal Blends 1-8% (w/v) alginate solutions in water were used; typically, 2-6% depending on the type and purity of alginate. Alginate solutions were prepared by magnetic stirring at room temperature
Cellulose nanocrystal (CNC) dispersions were prepared by magnetic stirring and ultrasonication at room temperature as follows:
1-6% (w/v) in water
Prepared by acid-hydrolysis of fully-bleached commercial kraft softwood pulp with 64 wt % sulfuric acid (8.75 mL of a sulfuric acid solution per gram of pulp) at 45° C. with vigorous stirring for 25 min
Surface modification of CNC was performed by TEMPO-mediated oxidation
Composite solutions of alginate and CNC were prepared by mixing with magnetic stirring at different concentrations of CNC with respect to alginate. The concentration of CNCs varied from 5-50%. The composite dispersions were prepared fresh before printing to avoid precipitation and hence inhomogeneity of concentration of CNCs.
The crosslinker solution comprised 50-125 mM Calcium Chloride in 1-5% PVA solution in water. Typically used 125 mM $CaCl_2$) in 2% PVA solution.
For bioprinting, alginate was ionically crosslinked with $Ca^{2+}$ during printing to create alginate fibers. TEMPO-modified CNCs possess surface carboxyl groups that helps them to get homogeneously dispersed in alginate solution and crosslinked via $Ca^{2+}$ ions resulting in alginate-CNC composite fibers.
For testing the tensile mechanical properties of this and other printed materials; fibres of alginate:CNC blends were 3D printed using a patented microfluidic extrusion device to generate multi-layered ring structures approximately 18 mm in external diameter, 1 mm wide and 1 mm high. Printed rings were loaded onto a UniVert (CellScale) mechanical testing device using custom hooks and subjected to increasing strain until the 3D-printed ring broke. Measurable parameters include peak stress at failure (Pa), tensile modulus (Pa), and tissue extension at failure (% original length).

Results—Inclusion of CNC with alginate did not significantly improve material tensile strength or flexibility.

Example 2: Printing with Alginate-Polyethylene Glycol Diacrylate (PEGDa) Blends 1-8% (w/v) alginate solutions in water were used; typically, 2-6% depending on the type and purity of alginate. Alginate solutions were prepared by magnetic stirring at room temperature
PEGDa solutions were prepared as follows:
Average molecular weight of PEGDa tested: 575 Da, 1 kDa, 3.4 kDa, 8 kDa, 10 kDa and 20 kDa
Concentration: 50-100% (w/v) in water
Solutions were prepared by dissolving liquid (PEGDa 575 Da and 1 KDa) or solid powder in water by magnetic stirring at room temperature
Photoinitiator, 2-Hydroxy-4'-(2-hydroxyethoxy)-2-methylpropiophenone (Irgacure 2959) was dissolved in PEGDa solution at concentrations 0.1-1.0% by magnetic stirring
The alginate and PEGDa blends were prepared as follows:
Alginate and PEGDa solutions containing photoinitiator were mixed by magnetic stirring at different concentrations of PEGDa with respect to alginate
Concentration of PEGDa varied from 50-100%
Composite solutions were prepared fresh before printing to avoid photodecomposition of PEGDa and photoinitiator
The crosslinker solution comprised 50-125 mM Calcium Chloride in 1-5% PVA solution in water. Typically 125 mM $CaCl_2$ in 2% PVA solution was used.
For printing followed by photocrosslinking: alginate was ionically crosslinked with $Ca^{2+}$ during printing to create alginate fibers while PEGDa remained uncrosslinked and embedded into the alginate fibers. After printing, crosslinking of PEGDa was attained by irradiating with 365 nm UV light for 5-40 min resulting in a second network. PEGDa with average molecular weight of 3.4 and 10 kDa were tested.

Discussion: To identify the PEGDA with appropriate MW that will give the optimal mechanical enhancement of the printed structures, we investigated PEGDA with MW ranging from 575 to 20,000 Da with printed alginate rings with 25 mm diameter and approximately 1 mm cross-sectional thickness (FIG. 1). Printed rings were soaked in 50% (w/v) PEGDA solution containing photo initiator overnight in the dark and crosslinked under UV light to generate the double network hydrogel (DNH). Photo-crosslinked alginate-PEGDA rings swelled when they were soaked in water. There was a general trend of increased swelling with the increase in the molecular weight of PEGDA used. The Alginate-PEGDA DNH rings were tested for their mechanical performance in tensile mode in a CellScale instrument, and the stress-strain curves are shown for DNH rings prepared with PEGDA of different MWs. Table 1 below summarizes the results of the tensile tests of these DNH rings:

TABLE 1

Tensile test data of alginate-PEGDA double network hydrogel rings

| Composition | Irradiation time (min) | Tensile Modulus (MPa) | Ultimate tensile strength (MPa) | Elongation at maximum stress (%) |
|---|---|---|---|---|
| Neat alginate | — | 0.21 ± 0.09 | 1.41 ± 0.67 | 462 ± 45 |
| Alg/PEGDA-575 | 10 | 0.94 ± 0.23 | 0.21 ± 0.09 | 32 ± 6 |
| Alg/PEGDA-1K | 10 | 1.56 ± 0.44 | 0.53 ± 0.18 | 69 ± 19 |
| Alg/PEGDA-3.4K | 10 | 1.17 ± 0.12 | 1.09 ± 0.23 | 115 ± 11 |
| Alg/PEGDA-8K | 10 | 0.16 ± 0.03 | 0.27 ± 0.07 | 226 ± 44 |
| Alg/PEGDA-10K | 12 | 0.23 ± 0.02 | 0.29 ± 0.06 | 140 ± 27 |

It is seen that rings printed with neat alginate show very high elongation at maximum stress (over 450%) and ultimate tensile stress of 1.41 MPa but rather low tensile modulus (0.21 MPa). Incorporation of PEGDA into the printed alginate rings resulted in reduction in strain and ultimate tensile stress but significantly increased the tensile modulus of DNH rings prepared with relatively low molecular weight PEGDAs. Among all of the DNH samples, Alginate-PEGDA rings prepared with PEGDA having average MW of 3,400 Da (PEGDA-3.4K) show the highest tensile modulus and ultimate tensile stress. Based on this mechanical strength data, PEGDA-3.4K was considered the most promising polymer to work with as it gives a stiffer material with similar maximum strength of neat alginate.

Example 3: Double Network Hydrogels of Alginate-Polyethylene Glycol Diacrylate (PEGDa) Blends by Post-Printing Impregnation of PEGDa into Printed Alginate Constructs Alginate, PEGDa and crosslinker solutions were prepared as above.

Certain blended compositions included CNC in the PEGDa/photoinitiator solutions. The concentration of CNC ranged from 5-50% of the weight of PEGDa.

Infiltration of PEGDa solution and photocrosslinking in printed ring structures and 3D-printed meniscus tissue was performed as follows: PEGDa solutions with or without CNC containing photoinitiator were poured onto the printed constructs drop by drop and allowed to soak in the dark overnight at room temperature (the concentration of PEGDa varied from 50-100%.) After overnight soaking, crosslinking of PEGDa in the printed constructs was attained by irradiating with 365 nm UV light for 5-40 min resulting in second network.

Mechanical Results—tensile strength was quantified using the UniVert instrument as above. Post-printing addition of alginate:PEGDa significantly impacted tensile properties, with 3.4 KDa PEGDa addition to LVM-alginate (low viscosity, high M) causing an increase in tensile modulus from 0.21±0.09 MPa to 1.17±0.12 MPa. The material with PEGDa was stiffer demonstrated by a reduced maximum elongation at break of 115% compared to LVM-alginate alone which extended to 462% of its original length before breaking. Maximum load at break were similar in LVM-alginate and LVM-alginate:PEGDa samples.

Figure 2:
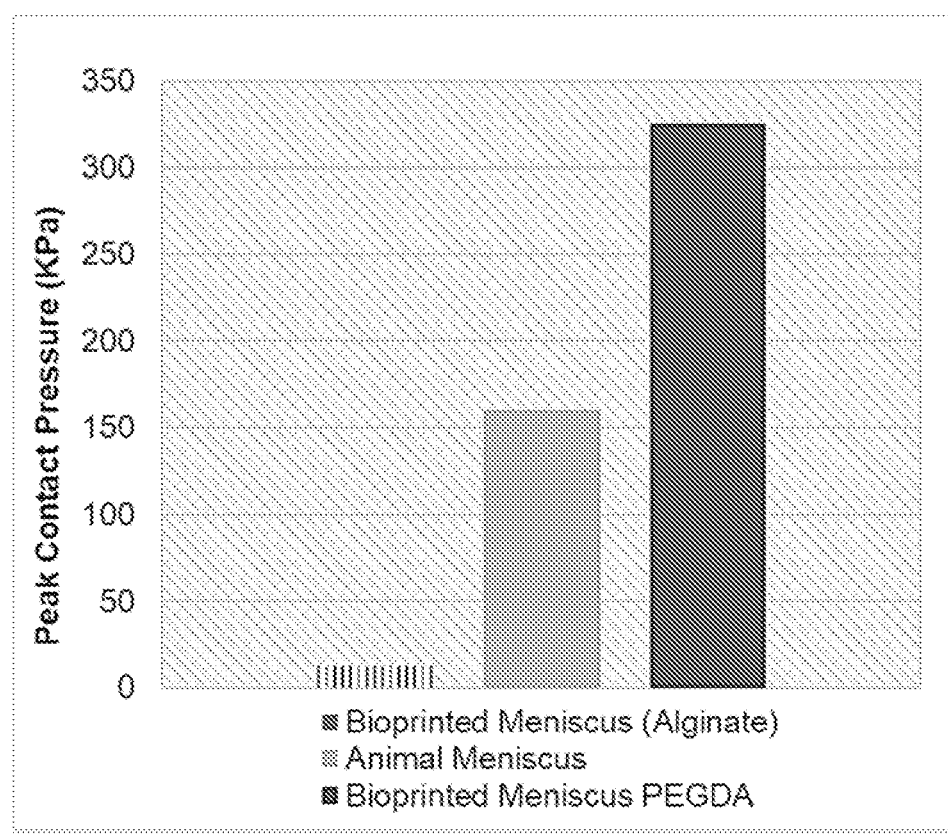
FIG. 2 is a graph showing the indentation strength of animal (sheep) menisci vs. bioprinted alginate menisci with or without PEGDA 3.4K as measured by the Peak Contact Pressure. As shown in the graph, the addition of PEGDA 3.4K increases the indentation strength of the alginate tissues.

Mechanical Results—compressive strength was quantified using the Mach-1 indentation instrument as above. In artificial meniscus tissues, post-print addition of PEGDa 3.4K to the apical surface of 3D-printed LVM-alginate and subsequent UV cross-linking, caused a significant increase in compressive strength from <20 kPa to >300 kPa. We demonstrate the post-printing addition of PEGDA 3.4K increases the peak contact pressure indentation strength of the alginate tissues to at least that of sheep menisci (FIG. 2).

Discussion—It proved challenging to cross-link PEGDA post-printing when it was blended and printed with alginate, we hypothesized this was because of diffusion of smaller Mw of PEGDA and the Irgacure® photoinitiator out of the blended mixture during printing. Instead, the addition of PEGDA to alginate fibres post-printing resulted in modulation of the tensile modulus, with smaller Mw PEGDA generating alginate structures that were stiffer but less elastic and brittle, with incorporation of higher Mw PEGDA resulting in softer gels that had lower tensile strength than the pure alginate. We also found that addition of 3.4 kDa PEGDA to printed alginate menisci generated a smooth and tough PEGDA gel coating on the apical surface which had a far higher compressive modulus compared to neat alginate menisci.

Example 4: Printing with Alginate-Polycaprolactone (PCL) Microspheres

Alginate and crosslinker solutions were prepared as above.

PCL microspheres were synthesized by oil-in-water (o/w) emulsion-solidification method. 1.5-3.0% (w/v) solution of PCL in dichloromethane (DCM) was used as dispersed phase while 1-5% (w/v) solution of poly (vinyl alcohol) (PVA) in water was used as continuous phase. The PCL solution was dispersed in PVA solution at 1:10 (v/v) ratio by magnetic stirring at 1200 rpm over 10 min. DCM was allowed to evaporate resulting in the solidification of the PCL microspheres at ambient condition by magnetically stirring the emulsion at 800 rpm in the fume hood for 6-8 hours. PCL microspheres were filtered through membranes and separated by centrifuge. This process reduces the polydispersity of the microspheres resulting in a mixture with a size distribution ranging from 5-50 μm. Microspheres of different sizes can be separated by filtration using membranes with a different width of pore opening. Reducing the level of polydispersity is essential to enabling high fidelity printing using microfluidic dispenser methods, as preparations with a broader size range cause blocking of the microfluidic channels.

Composite solutions of alginate and PCL microspheres were prepared by mixing respective solutions using magnetic stirring. The concentration of PCL microspheres varied from 1-5% (w/v). Composite dispersions were prepared fresh before printing to avoid precipitation and hence inhomogeneity of concentration of PCL microspheres. For printing, alginate was ionically crosslinked with $Ca^{2+}$ during printing to create alginate fibers.

Dissolution of PCL microspheres: printed constructs containing PCL microspheres embedded in the alginate fibers were solvent-exchanged from water to ethanol using a series of binary water/ethanol solvent mixtures. The water/ethanol mixtures used were: 100/0, 75/25, 50/50, 25/100, and 0/100. After solvent-exchange, the constructs were exposed to DCM vapor at room temperature for 10-30 min to dissolve PCL microspheres producing second network within alginate fibers. The constructs were rehydrated using water/ethanol mixtures in reverse order to that of solvent-exchange.

Discussion—In as-printed fibers, the PCL microspheres remained dispersed without any interconnected network and fell apart when the crosslinked alginate was removed e.g., by dissolving with EDTA. As a result, the incorporation of PCL MS into the alginate network did not improve the mechanical properties of the fibers. We then hypothesized that if PCL MS could be selectively melted/dissolved, it could form an interpenetrated secondary network of PCL within alginate matrix leading to the improvement of the mechanical strength of printed fibers. Upon selective dissolution and MS fusion with the solvent DCM, the polymer particles produced a co-continuous secondary network within the hydrogel framework resulting in composite fibers that had some favorable mechanical properties. Unfortunately, however, with moderate concentration (2.5%) of PCL microsphere loading into meniscus constructs, both suture retention strength and contact pressure decreased compared to the neat alginate menisci and these effects were exacerbated with increasing concentration. These results indicate that with increased PCL loading the printed structures become harder but brittle.

Example 5: Printing with Chitosan

Preparation of Chitosan and Crosslinker Solutions for Printing 2.5%-4.5% (w/v) solutions of low molecular weight chitosan (Sigma Aldrich, degree of deacetylation 77%) were made by dissolving chitosan powder in 2% (v/v) acetic acid with vigorous stirring over several hours. The crosslinker solution for the chitosan was prepared by dissolving 0.5%-5% of sodium tripolyphosphate (STP, Sigma Aldrich) in DI water together with 5% of polyethylene glycol (low viscosity crosslinker) or 15% of polyethylene glycol (high viscosity crosslinker) with MW=20000 (PEG20k, Alfa Aesar). The crosslinker was prepared by combining the appropriate volumes of a 16% (w/v) STP stock solution, a 30% (w/v) PEG20k solution prepared in DI water to make the desired final STP and PEG20k concentrations.

3D Printing Chitosan Using an STP Crosslinker

For 3D printing, the acidic chitosan solution and the STP-PEG-crosslinker were combined in the printhead to produce a solid fiber through ionic crosslinking of the positively charged amino groups in the chitosan polymer chain and the negatively charged phosphate groups in STP. 2% acetic acid was used as the buffer solution during printing to keep chitosan in acidic conditions and to prevent precipitation due to pH increase. For evaluating the mechanical properties of fibers produced with different chitosan and crosslinker formulations, ring-shaped structures were printed with the diameter of 15 or 20 mm and height and width of approximately 1 mm. Typical printing parameters used for rings were 300-1000 mbar pressure for the chitosan solution, 50-100 mbar pressure for the low viscosity crosslinker, 300-500 mbar pressure for the high viscosity crosslinker and 5-20 mm/s for printing speed. For the meniscus application, chitosan structures were printed according to a specific crescent-shaped meniscus model. For meniscus sample printing, typical printing parameters were 500-600 mbar pressure for the chitosan solution, 300-1000 mbar pressure for the high viscosity crosslinker and 18-22 mm/s for printing speed.

Measuring Material Strength Using Ring Tensile Tests

The mechanical performance of both freshly printed chitosan rings and rings hydrated with 0.9% (w/v) saline was evaluated by tensile tests. All experiments were performed in room temperature. The printed chitosan rings were loaded onto hooks on a mechanical tester (UniVert, CellScale, Waterloo, ON, Canada) and pulled until failure with the speed of 0.5 mm/s and a preload of 0.1 N. From the force-displacement data, the circumferential stress (MPa), Green strain (%), tensile modulus (MPa), ultimate tensile strength (MPa) and elongation at maximum stress (%) were calculated.

Results

Effect of Chitosan Concentration on Mechanical Performance

Figure 3:
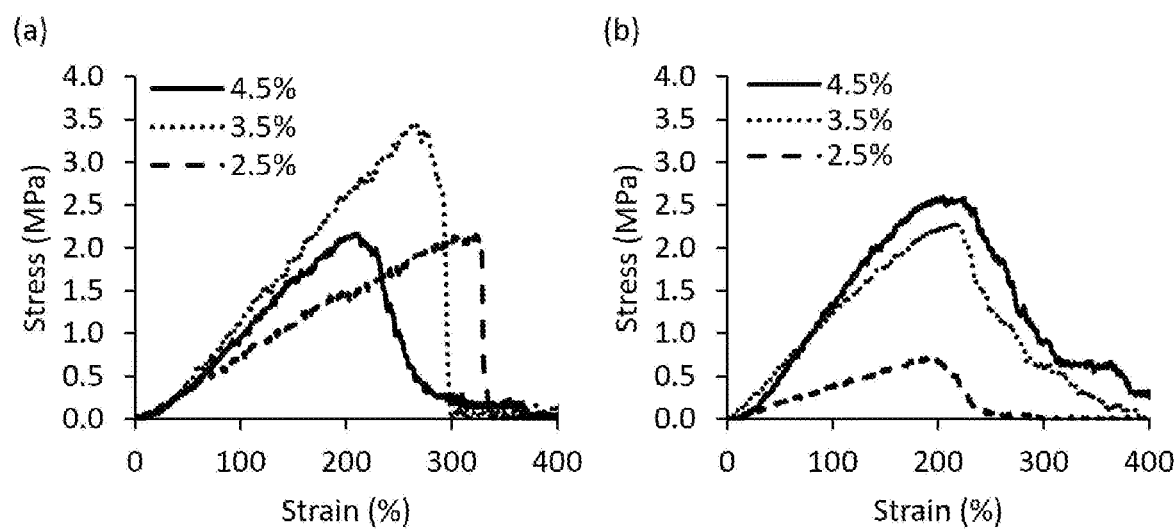
FIG. 3 shows the effects of chitosan concentration on tensile strength. Tensile properties of rings printed with 2.5% STP and 15% PEG20k with different chitosan concentrations (a) freshly printed and (b) after hydration in 0.9% saline.

The effect of chitosan concentration on the mechanical performance of printed rings was tested by varying chitosan concentration from 2.5%-4.5% while using a standard high viscosity crosslinker with 2.5% STP and 15% PEG20k. Both freshly printed rings and rings hydrated with 0.9% saline were tested. The results of the ring tensile tests are summarized in FIG. 3. Hydration with saline (FIG. 3b) slightly reduced the tensile modulus and drastically reduced the ultimate tensile strength for the lower chitosan concentrations of 2.5% and 3.5% compared to the freshly printed rings (FIG. 3a). In contrast, rings with the highest chitosan concentration of 4.5% retained their mechanical properties well in the hydrated state. In fact, the tensile modulus and the ultimate tensile strength of these rings slightly increased in the hydrated state compared to the freshly printed state. Increasing the chitosan concentration is thus beneficial from a mechanical perspective, which is likely due to the formation of a more crosslinked chitosan network and less swelling in aqueous medium. Higher chitosan concentration also makes the printed structures more stable in saline. For example, rings with 2.5% chitosan were fragile and easily unraveled in solution whereas 3.5% chitosan rings were more robust and did not unravel in saline. However, increasing the chitosan concentration also significantly increases viscosity and the higher viscosity solutions require a much lower speed to be used for printing (5 mm/s for 4.5% vs. 20 mm/s for 2.5% chitosan). The calculated values for the tensile modulus, ultimate tensile strength and elongation at maximum stress for the different chitosan concentrations tested are summarized in Table 2.

TABLE 2

Tensile properties of rings printed with 2.5% STP, 15% PEG20k and different chitosan concentrations.

| Chitosan | Crosslinker, STP %/ PEG20k % | State | Tensile modulus (MPa) | Tensile strength (MPa) | Elongation (%) |
|---|---|---|---|---|---|
| 2.5% | 2.5%/15% | As printed | 0.74 ± 0.09 | 2.12 ± 0.37 | 312 ± 20 |
| 3.5% | 2.5%/15% | As printed | 1.45 ± 0.33 | 3.02 ± 0.88 | 228 ± 33 |
| 4.5% | 2.5%/15% | As printed | 1.04 ± 0.12 | 2.11 ± 0.46 | 240 ± 81 |
| 2.5% | 2.5%/15% | Hydrated | 0.42 ± 0.03 | 0.73 ± 0.13 | 193 ± 13 |
| 3.5% | 2.5%/15% | Hydrated | 1.31 ± 0.06 | 2.54 ± 0.45 | 226 ± 34 |
| 4.5% | 2.5%/15% | Hydrated | 1.49 ± 0.19 | 2.30 ± 0.30 | 207 ± 20 |

Figure 4:
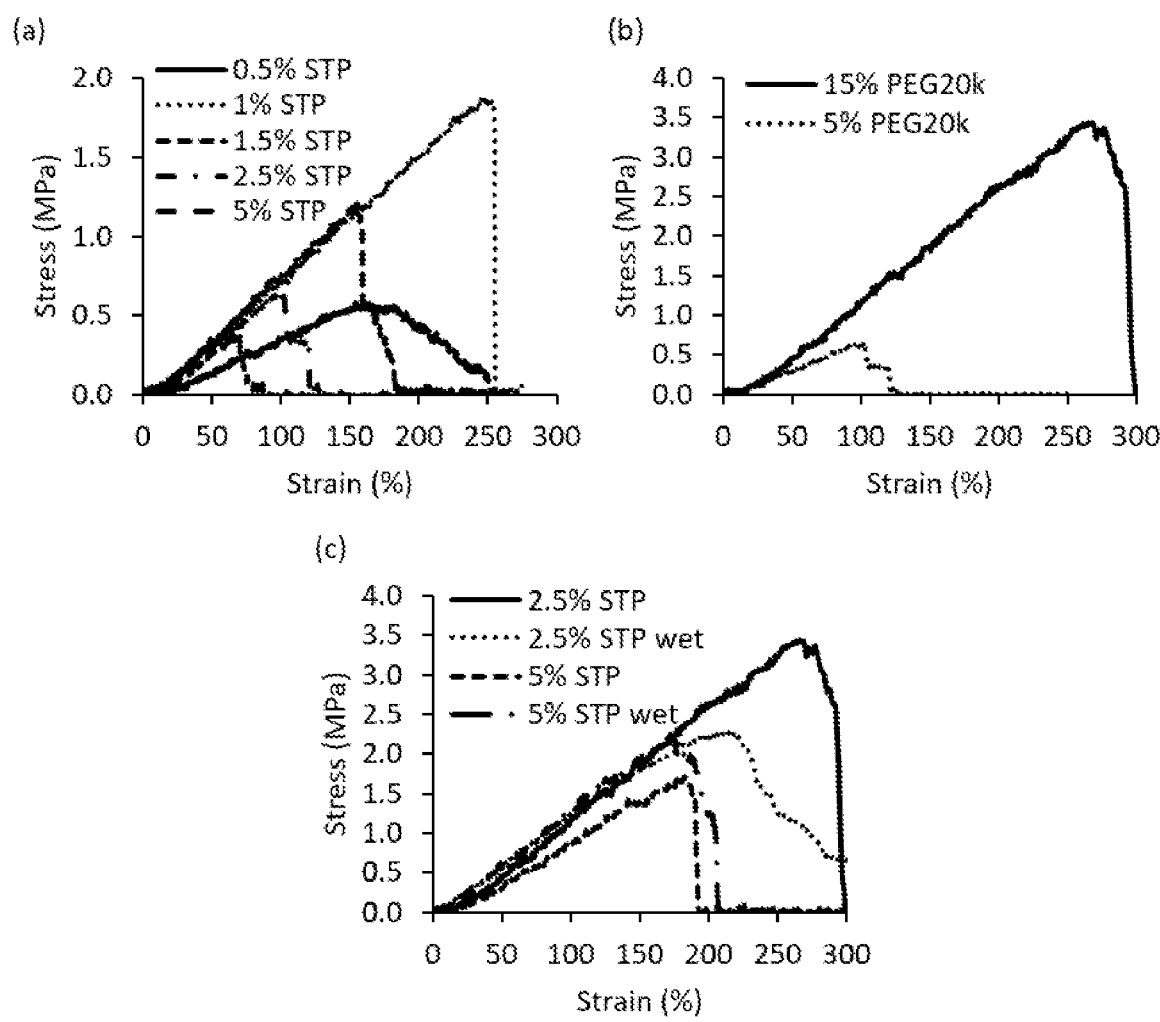
FIG. 4 shows the tensile properties of 3.5% chitosan rings (a) with 5% PEG20k and different STP concentrations, (b) with 2.5% STP and different PEG20k concentrations and (c) with 2.5% or 5% STP in 15% PEG20k either freshly printed or hydrated in saline ("wet").

Discussion—Effect of STP concentration and PEG concentration on mechanical performance. The composition of the STP-based crosslinker had a pronounced effect on the mechanical properties of printed chitosan rings. STP concentrations of 0.5-5% were tested with the low viscosity 5% PEG 20k crosslinker (FIG. 4a). Increasing the STP concentration from 0.5% to 1% significantly increased the tensile modulus, ultimate tensile strength and elongation of the 3.5% chitosan rings. Increasing the STP concentration further, however, made the rings more brittle and notably decreased their ultimate tensile strength and elongation. This could be due to increased degree of crosslinking leading to more brittle chitosan networks. This increased brittleness could be effectively counteracted by increasing the PEG concentration of the crosslinking from 5% to 15% (FIG. 4b). 2.5% was chosen as the STP concentration because with the high PEG concentration, structures printed with 1% STP were less stable and prone to unraveling in aqueous medium. Increasing the STP concentration to 5% did not lead to significantly improved mechanical performance in freshly printed or hydrated rings (FIG. 4c). All in all, the best mechanical performance with respect to both tensile modulus, ultimate tensile strength and stability in water was achieved with the high viscosity, 15% PEG20k crosslinker with 2.5% STP. The calculated values for the tensile modulus, ultimate tensile strength and elongation at maximum stress for the different chitosan and crosslinker formulations are summarized in Table 3.

TABLE 3

Tensile properties of rings printed with 3.5% chitosan and different crosslinker concentrations.

| Chitosan | Crosslinker, STP %/ PEG20k % | State | Tensile modulus (MPa) | Tensile strength (MPa) | Elongation (%) |
|---|---|---|---|---|---|
| 3.5% | 0.5%/5% | As printed | 0.41 ± 0.10 | 0.61 ± 0.21 | 171 ± 16 |
| 3.5% | 1%/5% | As printed | 0.76 ± 0.11 | 1.78 ± 0.12 | 249 ± 18 |
| 3.5% | 1.5%/5% | As printed | 0.82 ± 0.11 | 1.26 ± 0.10 | 172 ± 20 |
| 3.5% | 2.5%/5% | As printed | 0.69 ± 0.10 | 0.65 ± 0.01 | 109 ± 22 |
| 3.5% | 5%/5% | As printed | 0.66 ± 0.03 | 0.38 ± 0.03 | 74 ± 5 |
| 3.5% | 2.5%/15% | As printed | 1.45 ± 0.33 | 3.02 ± 0.88 | 228 ± 33 |
| 3.5% | 2.5%/15% | Hydrated | 1.31 ± 0.06 | 2.54 ± 0.45 | 226 ± 34 |
| 3.5% | 5%/15% | As printed | 1.07 ± 0.22 | 1.51 ± 0.17 | 164 ± 37 |
| 3.5% | 5%/15% | Hydrated | 1.37 ± 0.17 | 2.28 ± 0.28 | 180 ± 13 |

Figure 5:
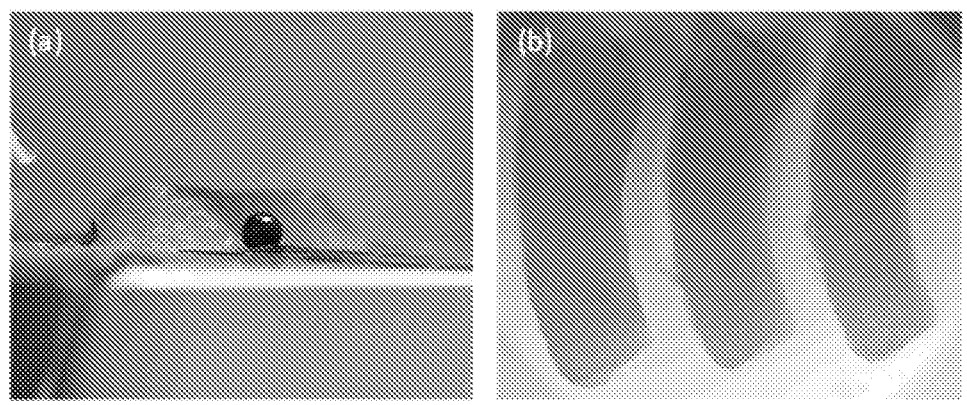
FIG. 5 shows meniscus samples printed with 3.5% chitosan and 2.5% STP in 15% PEG20k from (a) the side and (b) from top. The diameter of the size reference ball is 2.4 mm (3/32").

Chitosan meniscus samples were printed using the 3.5% chitosan and 2.5% STP in 15% PEG20k (FIG. 5). The printed structures replicated the 3D meniscus design well, with an average height and width of 4 mm and 9 mm, respectively (4 mm and 8 mm in 3D meniscus design).

Example 6: Printing with Chitosan-Poly (Vinyl Alcohol) (PVA) Blends

Chitosan-PVA blends were prepared by combining an acidic chitosan solution and a PVA solution in the desired ratio (w/w). 3%, 3.5% or 4.5% (w/v) solutions of low molecular weight chitosan (Sigma Aldrich, degree of deacetylation 77%) in 2% (v/v) acetic acid were combined in specific ratios with an either 10% or 15% PVA solution (PVA MW 146000-186000, 99+% hydrolyzed, Sigma Aldrich). The PVA solutions were prepared by autoclaving (121° C., 100 kPa or 50 kPa) for 15 min.

Printing, Post-Processing and Mechanical Testing of Chitosan-PVA Blends

The chitosan-PVA blends were printed using the standard crosslinker for pure chitosan, namely a solution with 2.5% STP and 15% PEG20k. 2% acetic acid was used as the buffer solution. Ring samples with 15 mm diameter and 1 mm height and width were printed for the mechanical testing of different blends. The compositions of the different blends as well as the parameters used for printing ring samples are summarized in Table 4 below.

TABLE 4

Compositions and parameters used for printing chitosan-PVA rings samples.

| Chitosan | PVA | Chi:PVA ratio (w/w) | Material pressure (mbar) | Crosslinker pressure (mbar) | Speed (mm/s) |
|---|---|---|---|---|---|
| 3.5% | 10% | 1:1 (50:50) | 800 | 350 | 18 |
| 3.5% | 12.5% | 1:1 (50:50) | 800 | 300 | 10 |
| 3.5% | 15% | 1:1 (50:50) | 800 | 300 | 5 |
| 4.5% | 15% | 1:1 (50:50) | 800 | 350 | 5 |
| 4.5% | 15% | 1.5:1 (60:40) | 800 | 350 | 5 |

During printing, chitosan in the blend was ionically crosslinked and solidified by STP. In order to crystallize and solidify the PVA (1), printed chitosan-PVA samples were subjected to repeated cycles of freezing in −70-80° C. and thawing in room temperature. A typical freeze-thaw cycle comprised 15 min of freezing and 30 min of thawing. Samples were subjected to a total of five freeze-thaw cycles and then hydrated in 0.9% saline. Hydrated samples were tested for tensile properties using the UniVert mechanical tested (CellScale, Waterloo, ON, Canada) using the same protocol as for pure chitosan samples. In addition to tensile properties, the recovery of the chitosan-PVA ring samples was also evaluated by releasing the samples from the hooks and by comparing the stretched size to the original sample size.

For the meniscus application, chitosan-PVA structures were printed using a blend of either 3.5% chitosan and 10% PVA 1:1 (lower viscosity) or 4.5% chitosan and 15% PVA 1:1 (higher viscosity). Different infill patterns were also tested. Square patterns were printed with either 12% or 7% infill and diamond, triangle and tringle+diamond patterns were printed with 7% infill. The typical printing parameters used meniscus sample printing with the different material compositions are summarized in Table 5.

TABLE 5

Compositions and parameters used for printing chitosan-PVA meniscus samples.

| Chitosan | PVA | Chi:PVA ratio (w/w) | Material pressure (mbar) | Crosslinker pressure (mbar) | Speed (mm/s) |
|---|---|---|---|---|---|
| 3.5% | 10% | 1:1 (50:50) | 1100 | 600 | 20 |
| 4.5% | 15% | 1:1 (50:50) | 950 | 300 | 7 |

Results

Effect of Freeze-Thawing on Mechanical Performance

Figure 6:
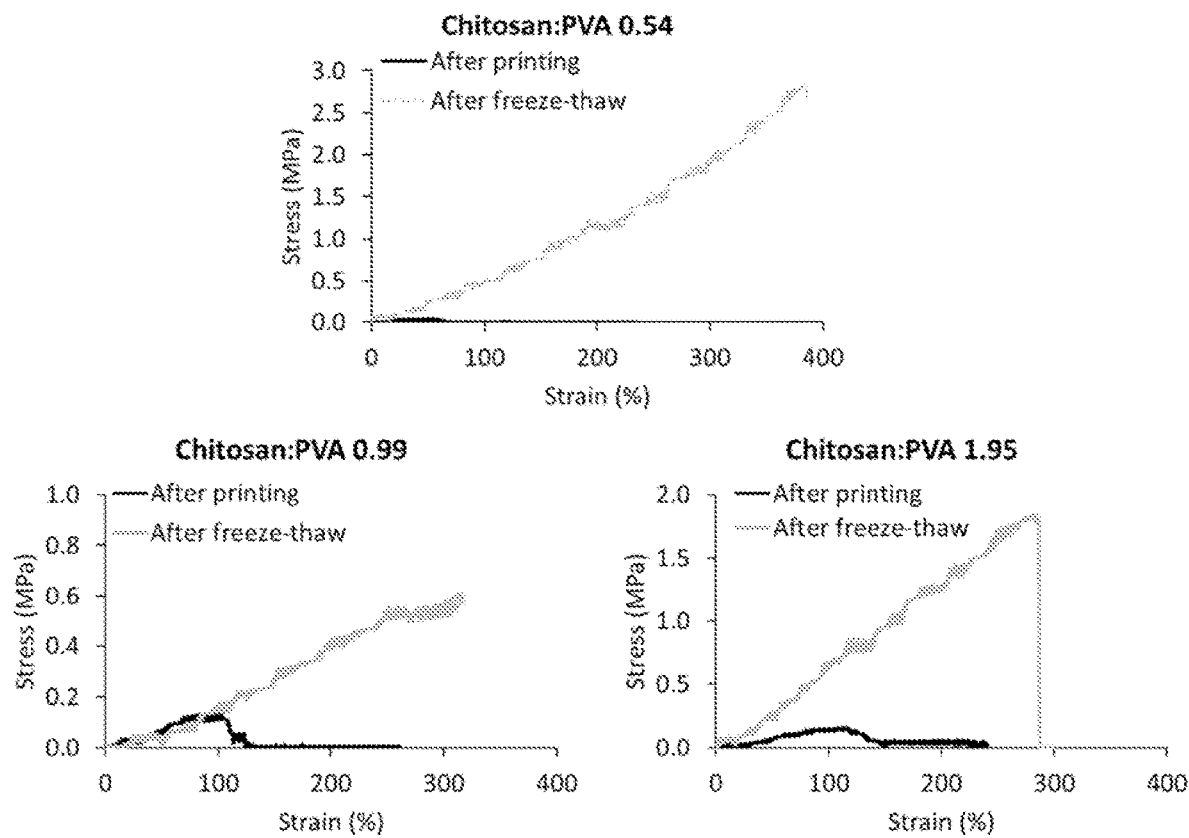
FIG. 6 provides three graphs looking at the tensile strength of chitosan:PVA fibers using various Chitosan:PVA ratios as indicated; the freeze-thaw cycles caused the PVA to crystalize and form a tough network as shown by increases in maximum stress in all chitosan:PVA ratios when freeze-thawed. The maximum stress was 3-80 fold increased with PVA freeze-thaw vs. chitosan alone.

The tensile properties of printed chitosan-PVA rings were improved significantly by exposing to cycles of freeze-thaw (FIG. 6). The tensile strength of printed rings with three different ratios of chitosan:PVA blends were tested before and after freeze-thawing, in all cases exposure to freeze-thaw cycles significantly increase ultimate tensile strength and the elongation at break.

Effect of Blend Composition on Mechanical Performance

Figure 7:
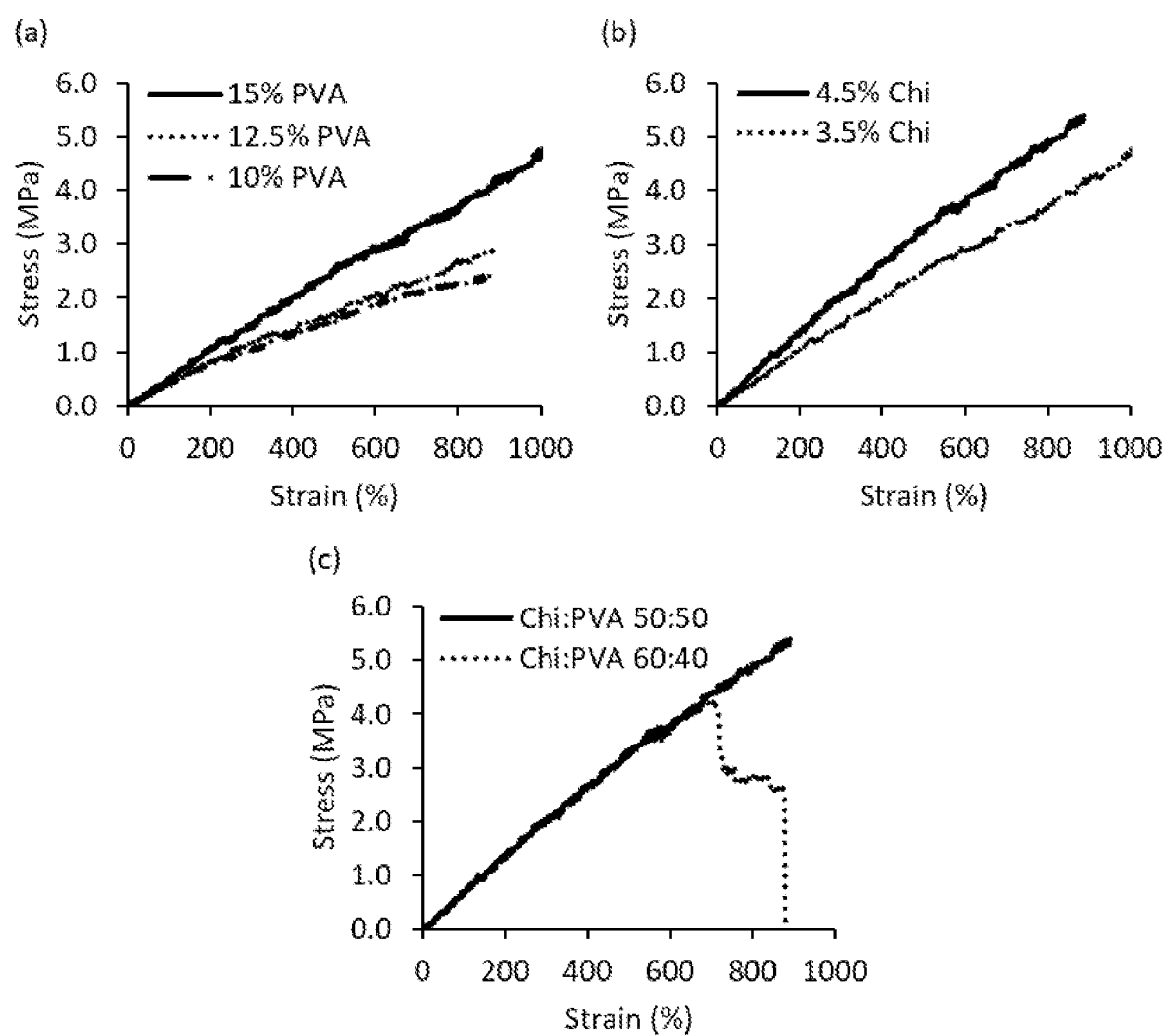
FIG. 7 shows the tensile properties of printed chitosan-PVA rings. (a) 3.5% chitosan combined with 10, 12.5, or 15% PVA, chi:PVA=1:1 (w/w), (b) with 3.5% or 4.5% chitosan combined with 15% PVA, chi:PVA=1:1 (w/w) and (c) with 4.5% chitosan combined with 15% PVA in a chi:PVA ratio of either 50:50 or 60:40 (w/w).

The tensile properties of printed chitosan-PVA rings were affected by the chitosan and PVA concentration in the blend, as well as the ratio of chitosan to PVA (FIG. 7). By increasing either the PVA concentration or the chitosan concentration, both the tensile modulus and the ultimate tensile strength of the printed structures could be significantly increased. Increasing the concentration of the PVA stock solution from 10% to 15%, increased the tensile strength of the printed rings by nearly 100% (FIG. 7a). Correspondingly, by increasing the chitosan stock concentration from 3.5% to 4.5% while keeping the PVA stock concentration at 15%, the tensile strength could be increased further by almost 25% (FIG. 7b). Finally, if the chitosan amount in the blend was increased by 10% compared to PVA, the printed structures became less elastic and the tensile strength was reduced by 30%. Based on these results, the optimal blend composition was chosen as 4.5% chitosan combined with 15% PVA in a ratio of 1:1 (w/w)

In addition to high tensile strength and elasticity, the chitosan-PVA blends also exhibited remarkable recovery after tensile deformation. Rings printed with the 3.5% chitosan and 10% PVA recovered almost to their original size (92%±2% recovery, n=5) with only minor damage after deformation with nearly 1000% strain.

Printing Meniscus Samples Using Chitosan-PVA Blends

Meniscus samples with high infill (>65%) were printed using the blend with 3.5% and 10% PVA 1:1 (FIG. 40). This lower viscosity blend was chosen because a higher printing speed could be used compared to the higher concentration blend (20 mm/s vs. 7 mm/s). The printing times of the high infill meniscus samples could this be shortened to approximately 1 h.

The printed meniscus samples replicated the 3D meniscus design relatively well but were somewhat larger in width especially. The average height and width of the samples were 4.2 mm±0.4 mm and 10.6 mm±0.5 mm (n=4), respectively compared to 4 mm and 8 mm in 3D meniscus design.

Discussion: Incorporation of PVA as a secondary matrix with chitosan increased the mechanical properties of chitosan fibers, with a significant increase in tensile strength and elasticity. Interestingly these mechanical parameters can be modulated by adjusting the concentration and ratios of the chitosan and PVA. The main limitation of the printed high infill chitosan-PVA menisci was the overall softness and the weak fiber-to-fiber adhesion highlighted in subsequent cadaver lab tests described below.

Example 6: Cadaver Lab Testing

Figure 8:
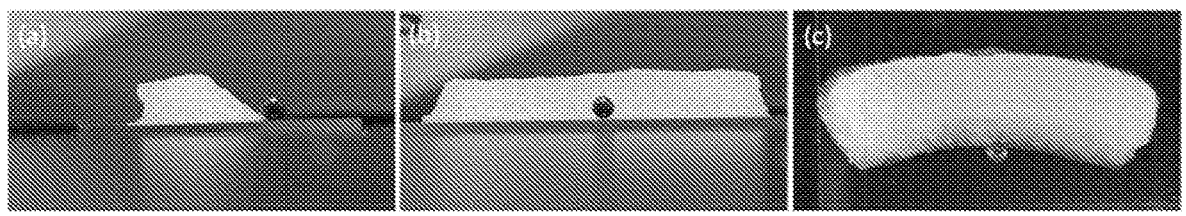
FIG. 8 shows printed chitosan-PVA meniscus samples, from (a, b) a side view and (c) from the top. The diameter of the size reference ball is 2.4 mm (3/32").

Four meniscus tissue types were used for the cadaver tests including; chitosan only (printed 3.5% chitosan), chitosan+PVA (polymerised PVA from 5× freeze/thaw cycles), alginate+PCL (PCL microspheres fused using DCM), and alginate+PEGDA (PEGDA cross-linked using UV). Prior to performing the cadaver lab tests, similar meniscus samples were tested for suture pull-out strength and indentation strength and the data plotted (FIG. 8). Chitosan only, chitosan+PVA and Alginate+PCL samples all met the suture retention strength target of 20 N, but demonstrated lower compressive strengths than the target of 100 kPa. Tissues consisting of printed Alginate with a secondary PEGDA matrix and post-printing UV cross-linking step, reached the suture pull-out target, and exceeded the compressive strength target by around 30 kPa. We observed that when SPO is plotted against indentation strength, in general there is an inverse correlation between the two values, samples with the greatest suture retention are softer in compression and vice versa. We hypothesize that this was because the SPO is a type of tensile test, fibres are being stretched as the suture is pulled from the tissue, therefore structures that contain flexible elastic fibres that are strong in tension are able to withstand greater suture pull-out forces than inelastic stiffer fibres. However, the elastic flexible fibres tended to result in a structure that was also easily deformable and therefore softer in compression.

The cadaver lab used a whole cadaveric human knee joint to assess the surgical suitability of the artificial menisci tissues. Experiments were performed to confirm the tissues could be trimmed to size, shuttled into the joint, surgically manipulated in the joint, and sutured into the peripheral meniscus remaining in the joint. Prior to implantation a keyhole access point was cut into the skin of the joint and the knee cavity was flushed. After cleaning of the interior of the joint, the lateral meniscus of the knee was trimmed to leave just the peripheral portion of the tissue intact. The defect space in the meniscus was measured with a specialized measuring device, and scissors or a scalpel blade were used to trim the replacement menisci down to the appropriate size. Replacement menisci tissues were shuttled into the joint through the keyhole in the skin using a tissue clamp. An "L"-shaped probe was used to further manipulate the tissue to position and orient it into the correct position in the joint in relation to the remaining peripheral meniscus tissue. The artificial tissues were sutured to the peripheral meniscus using ethibond 2-0 suture material. Vertical and horizontal loop sutures were tested to secure the implant to the peripheral meniscus tissue. Six test implantations were performed in sequence into the same knee with the sequence of the tissues testing listed below (Table 6).

TABLE 6

Cadaveric knee test number and meniscus prototype composition.

| Test # | Tissue # | Tissue composition |
| --- | --- | --- |
| 1 | A1 | 3.5% chitosan |
| 2 | B1 | 3.5% chitosan + PVA (printed mixed fibers) |
| 3 | C1 | DH alginate + 3.4K PEGDA |
| 4 | D1 | DH alginate + PCL |
| 5 | D2 | DH alginate + PCL |
| 6 | C3 | DH alginate + 3.4K PEGDA |

In all cases, the tissues could be trimmed to size and were shuttled successfully into the joint cavity. However, once in the fluid-filled joint and exposed to physical stress, tissue delamination was a common problem although the chitosan+PVA sample suffered less than other tissues. Several tissue types including, chitosan, chitosan+PVA and Alginate+PEGDA could be successfully sutured. Chitosan+PVA (test #1) and alginate+PEGDA (test #3 & #6) had the most stable sutures. Tissue softness was also an issue, with chitosan-only and chitosan+PVA tissues being too soft to manipulate easily in the joint cavity. Alginate+PEGDA had a tougher upper surface which was attractive, but delamination occurred at the interface between the alginate and the cap of PEGDA that was restricted to the surface of the high density structure. Although the cadaver lab clearly demonstrated that our printed meniscus tissues were capable of achieving our primary goal of suture retention, the surgical observations were essential to guide the future development of the meniscus tissue.

Example 7—Printing Fiber+Cast Matrix Composite Tissues

Based on the cadaver lab results above, we explored the potential for fabricating composite tissues consisting of a printed framework of fibers surrounded by a cast matrix, in an order to generate meniscus samples that achieved all three of the mechanical deliverables, suture pull-out strength (20N), indentation strength (100 kPa) and tensile strength (1 MPa). We hypothesized that the printed meshwork would contribute to tensile strength and suture pull-out resistance, while a secondary cast hydrogel matrix would synergise with the fiber network to improve stability and shear strength via increased fiber-fiber and inter-layer bonding, as well as increasing compressive strength to generate a more functionally appropriate tissue, similar to the effect of steel-reinforcing rods in concrete. We had already attempted this to some extent with the secondary addition of PEGDA to printed alginate constructs with a high fiber in-fill density (800%), but observed a lack of penetration of the secondary network into the printed structure, resulting in an outer coating of PEGDA gel with a plane of cleavage between the PEGDA and alginate, leading to delamination between the cast and printed components. In JSC #12 we discussed potential strategies for improving secondary matrix penetration into printed tissues, including the fabrication of printed networks of fibers at a lower in-fill density for subsequent infusion via centrifugation or vacuum. We used our custom tissue design software to generate tissues with rectilinear fiber deposition at in-fill densities of between 7% and 5. We tested chitosan-only fibers, and chitosan+PVA printed fibers, in combination with a secondary cast matrix of PEGDA, cellulose nanocrystals (CNC), or PVA. The mechanical performance of composite tissues were quantified using suture pull-out, tensile, compressive and lap-shear mechanical tests. Results were directly compared to non-composite printed tissues without a secondary matrix printed at a high in-fill density (7000 average), and to cast hydrogel tissues of pure PVA (Table 7)

achieving the indentation strength, however the cast-PVA tissues were below the target tensile strength of 1 MPa. Lap-shear tests demonstrate that the DH-alginate printed-only tissue had a 5× reduction in shear-strength when hydrated in saline. This result mirrored the cadaver lab observations where printed tissues (particularly alginate-based tissues) delaminated when fully hydrated in the saline-filled knee joint. In contrast, the composite tissue of chitosan & PVA fibers, with a secondary network of cast PVA matrix, demonstrated over 150× increase in shear strength vs the hydrated alginate sample (164 kPa vs. 1 kPa). This data highlights the challenge of preventing inter-layer delamination in tissues that contain only printed fibers, and suggests that using a secondary cast matrix to generate a composite tissue is one approach to increase the stability of the printed structure. Below we describe in more detail the studies we performed to demonstrate the mechanical benefits of the composite tissue approach by performing in-depth studies to directly compare the mechanical properties of; printed mesh, cast, and composite tissues.

Example 8: Chitosan-PVA+PEGDa Composite Meniscus Tissues

PEGDA:alginate blends were demonstrated to have beneficial effects on alginate hydrogel strength in ring tensile tests, and PEGDA added as a secondary matrix to the surface of printed alginate menisci with a high fiber in-fill density (80%) was also observed to have some positive impact on

TABLE 7

Composite vs. non-composite tissue mechanical characteristics

| Printed Material | Secondary material | Toolpath | SPO (N) *20N | Indentation (kPa) *100 kPa | Tensile (Mpa) *1.0 MPa | Lap shear (kPa) |
|---|---|---|---|---|---|---|
| DH alginate | PVA:CNC | 80% concen 60% rectilin | 8.7 | 42.5 | — | 5.1 (dry) 1.0 (hydrated) |
| DH alginate | 3.4K PEGDA centrifuged | 80% concen 60% rectilin | 21.1 | 132 | 0.56 | |
| 1:1 Chitosan (4.5%) PVA (15%) | PVA (20%) centrifuged | 12% rectilin (vertical/horizontal) | 59 | 110 | 1.51 | 164.1 (hydrated) |
| 1:1 Chitosan (4.5%) PVA (15%) | 3.4K PEGDA centrifuged | 12% rectilin (vertical/horizontal) | 32.7 | 303 | 0.96 | |
| 1:1 Chitosan (4.5%) PVA (15%) | None | 12% rectilin (vertical/horizontal) | 40.8 | 23.9 | 0.97 | |
| 1:1 Chitosan (3.5%) PVA (10%) | None | 80% concen 60% rectilin | 52 | 31.0 | 1.17 | |
| Chitosan (3.5%) | None | 80% concen 60% rectilin | 34.6 | 41.2 | — | |
| Chitosan 3.5% | PVA 15% | 12% rectilin | 24.4 | 51.6 | — | |
| None | PVA (20%) | NA-Cast | 25.6 | 93.05 | 0.66 | |

During our subsequent studies it quickly became apparent that CNC gels do not improve mechanical performance, and PEGDA was challenging to cross-link in larger tissues using photo-activation of photoinitiators. Composite tissues with combinations of printed chitosan+PVA fibers with a secondary matrix of cast PEGDA (3.4 kDa) or PVA were the only tissues that achieved the three mechanical targets of suture retention, indentation and tensile strengths. Tissues that contain only printed fibers of chitosan or chitosan+PVA, tended to achieve the suture retention and tensile targets, but failed to reach the target indentation strength of 100 kPa, even at high in-fill densities. The cast PVA-only tissues achieved the target suture retention and were very close to tissue compressive strength and usability in the cadaver test. The chitosan:PVA printed fiber tissues demonstrated the strongest tensile strength and suture pull-out strength, thus to overcome the limitations of printed chitosan-PVA meniscus samples, namely softness and weak fiber-to-fiber adhesion, we decided to combine a lower density printed porous mesh of chitosan:PVA with a secondary matrix of PEGDA that penetrated throughout the printed structure Since, the freeze-thaw treatments resulted in opaque tissue scaffolds, photo-mediated PEGDA cross-linking was inappropriate, thus we used ammonium persulfate (APS) and tetramethylethylenediamine (TEMED) to crosslink PEGDA inside the chitosan-PVA mesh structure via direct free radical release.

Materials & Methods

Chitosan solution was prepared by dissolving required amount of powdered chitosan in 2% acetic acid solution by magnetic stirring. Poly (vinyl alcohol) (PVA) solutions (2-3% w/v) were prepared by dissolving required amount in deionized water by magnetic stirring at 60° C. Higher concentration PVA solution was prepared by autoclaving the mixture of PVA and water for 15 min at 121° C.

Infiltration of PEGDA into chitosan-PVA meniscus: Rectilinear menisci frameworks (Ch-PVA mesh) were printed with low (12%) infill density using a similar composite chitosan-PVA strategy to previous experiments. Briefly, a solution containing equal weight fraction of 4.5% (w/v) LMW chitosan solution and 15% (w/v) PVA solution. 2.5% (w/v) sodium tripolyphosphate solution (STP) in 15% PEG-20K was used as crosslinker to generate fibres. Printed menisci samples were treated by freezing for 15 min at −75° C. to −80° C. and thawing at room temperature for 30 min. After five freeze-thaw cycles, menisci samples were dried under vacuum for 3 h. Menisci printed with ~25 mm circumferential length (for indentation and SPO tests) were impregnated with 300 μl of 150% (w/v) PEGDA-3.4K solution mixed with 7 μl of 0.625 M TEMED and 7 μl of 1.25 M APS solution dropwise and allowed to soak and crosslink for 3 h in a closed container. PEGDA crosslinked menisci samples were then immersed in water to remove unreacted reagents for 15 min and in 0.9% saline for 2 h. Finally, the chitosan-PVA-PEGDA menisci samples were stored in custom-made water vapour container until tested for mechanical properties. Menisci printed with ~40 mm circumferential length (for tensile tests) were impregnated with 600 μl of 150% (w/v) PEGDA-3.4K solution mixed with proportional volume of TEMED and APS solution. The rest of the procedure remained identical.

Results

Figure 9:
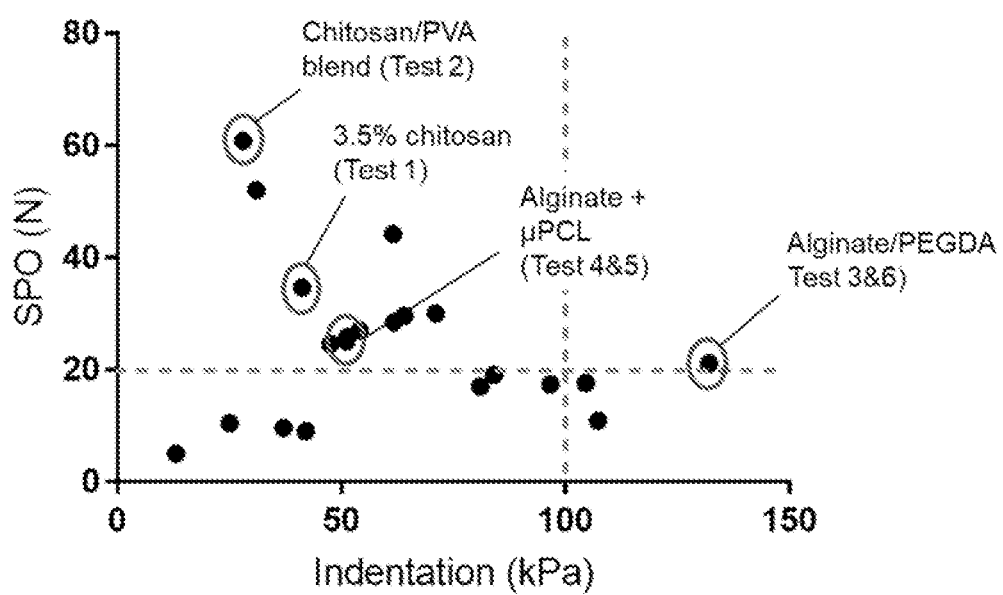
FIG. 9 shows the relative Suture Pull-Out (SPO) and indentation strength plots for multiple bioprinted meniscus types. The four research prototypes are circled in green. All were selected as they reached the SPO target (20N). Only one tissue (alginate+PEGDA) achieved the target for both SPO and compressive tests.

Chitosan-PVA fibers were printed into menisci structures with low infill density of the printed fibres (12%). After five freeze-thaw cycles to promote the physical crosslinking of PVA, the printed chitosan:PVA constructs rendered highly porous menisci scaffolds which were successfully penetrated by a secondary matrix of PEGDA-3.4K which was subsequently cross-linked with APS/TEMED to generate chitosan:PVA-PEGDA composite menisci (FIG. 9).

Mechanical tests demonstrate that the chitosan:PVA-PEGDA composite tissues successfully exceeded the suture pull-out target with a SPO value of 32.7 N, the compressive strength was more than an order of magnitude greater than the chitosan:PVA mesh alone, and exceeded the secondary compressive strength target at 303 kPa, and the tensile strength of the chitosan:PVA-PEGDA composites were very close to the target, at 0.96 MPa (Table 7).

Example 9—Printing Chitosan-PVA+PVA Composite Meniscus Tissues

We developed a second strategy to combine a printed, porous mesh structure with cast PVA as a secondary matrix, since PVA hydrogels have a water content and viscoelasticity that is very similar to human menisci. For these studies we used a PVA concentration of 20% for the secondary matrix as a compromise between increasing stiffness while maintaining low enough viscosity for handling the solution. PVA solutions with concentrations of 25% and 30% were considered too viscous to be efficiently incorporated into the printed mesh.

Materials & Methods

For the preparation of chitosan:PVA mesh with cast PVA composite menisci, chitosan:PVA fiber structures with relatively low infill (7% or 12%) were first printed using the blend of 4.5% low molecular weight chitosan (Sigma Aldrich, degree of deacetylation 77%) in 2% (v/v) acetic acid combined in specific ratios with either 10% or 15% PVA solution (PVA MW 146000-186000, 99+% hydrolyzed, Sigma Aldrich). After printing, the fiber structures were subjected to five freeze-thaw cycles and then dried under vacuum for 30 min-1 h. After drying, the samples were immersed in a 20% PVA solution of the same type as used for printing, and centrifuged at 2000 rpm for 10 min to fully infiltrate the PVA within the porous printed structure. After centrifuging, the samples were removed from the viscous PVA solution and subjected to five more freeze-thaw cycles before hydration in 0.9% saline. The composite menisci thus comprised a printed, chitosan-PVA fiber mesh and a solid 20% PVA matrix encasing the printed fibers. Cast PVA tissues were gen To quantify the ratios of the printed chitosan-PVA fibers, PVA matrix and the incorporated water in the composite menisci, the printed mesh was fully hydrated in saline and the wet mass measured. This was followed by drying under vacuum overnight and the measurement of dry mass. The dried samples were briefly rehydrated in saline (15 min) and then put under vacuum for 30 min before incorporating the 20% PVA matrix by centrifuging. After freeze-thaw cycling and hydration in saline, the wet mass of the composites was measured. Finally, the composite samples were dried under vacuum overnight and the dry mass was measured.

Figure 10:
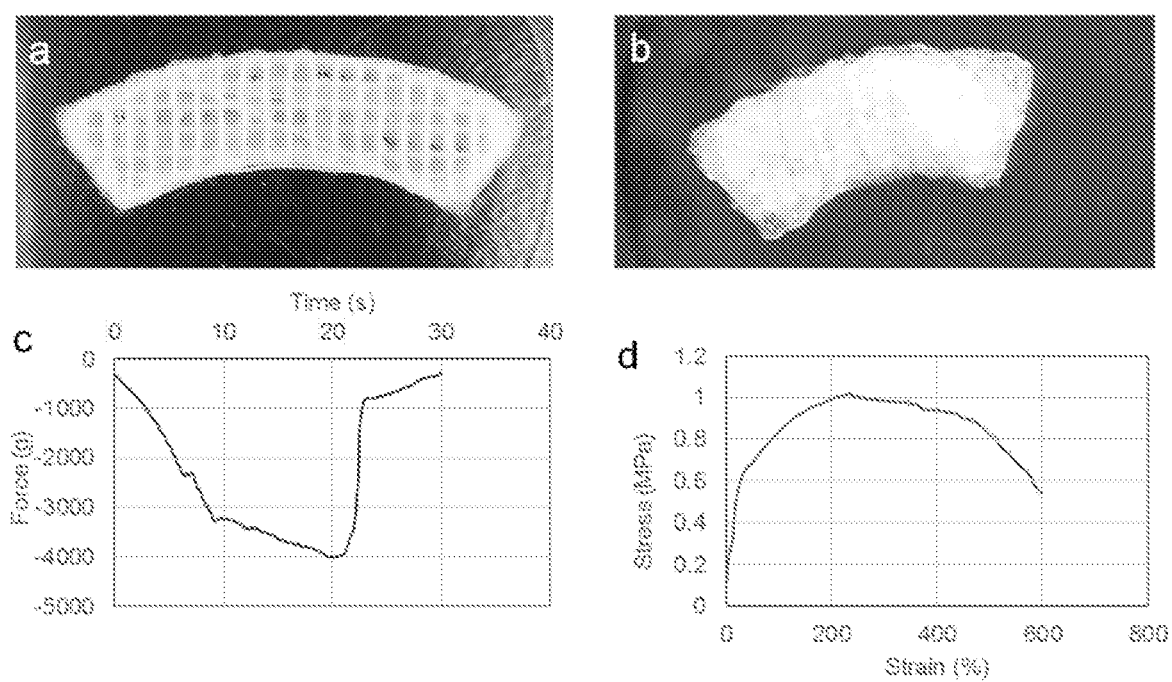
FIG. 10 shows the printing of chitosan-PVA with PEGDA added as a secondary material. a) Photograph showing a rectilinear meniscus scaffold printed with Chitosan-PVA after five cycles of freeze-thaw, b) composite meniscus after incorporation and crosslinking of PEGDA-3.4K with APS/TEMED, c) a typical force-time curve obtained from suture pull out tests, and d) a representative stress-strain curve from tensile test of Chitosan-PVA-PEGDA-3.4K meniscus.

The measured strut size of the printed mesh structures was approximately 300 μm. Due to the addition of the PVA matrix, the composite menisci had a smooth, slippery surface and they were mechanically much more stiff and robust than the printed mesh structures alone. The final dimensions of the composite meniscus samples were about 20% larger than the designed values. The average height and width were 4.6 mm±0.1 mm and 9.5 mm±0.4 mm (n=6), respectively, which are still relatively close to the target values (4 mm for height and 8 mm for width) (FIG. 10).

Results a. Analysis of Chitosan:PVA-PVA Tissue Composition

We performed experiments to measure the volume, dry weight and hydrated weight of the chitosan:PVA composite tissue to calculate the relative % contribution of printed fiber, secondary matrix and water, to the overall composition of the tissue. Based on the results, the total amounts of water, fiber and matrix in the composites could be calculated. The composites contained 74%±3% water, calculated by comparing the mass of the incorporated water to the total hydrated composite mass. This corresponds well to the native meniscus that is reported to contain 72%-78% water (Bryceland 2017, Bilgen 2018). Correspondingly, the composites contained approximately 26% polymer by total weight. Of this total polymer amount, the printed chitosan-PVA fibers and the PVA matrix make up 39%±4% and 61%±4%, respectively (w/w, dry). In summary, the composite menisci contained approximately 74% water and 26% polymer in which the ratio of fiber-to-matrix was approximately 40/60.

b. Comparison of Mechanical Strength of Cast, Printed and Composite Tissues.

Figure 11:
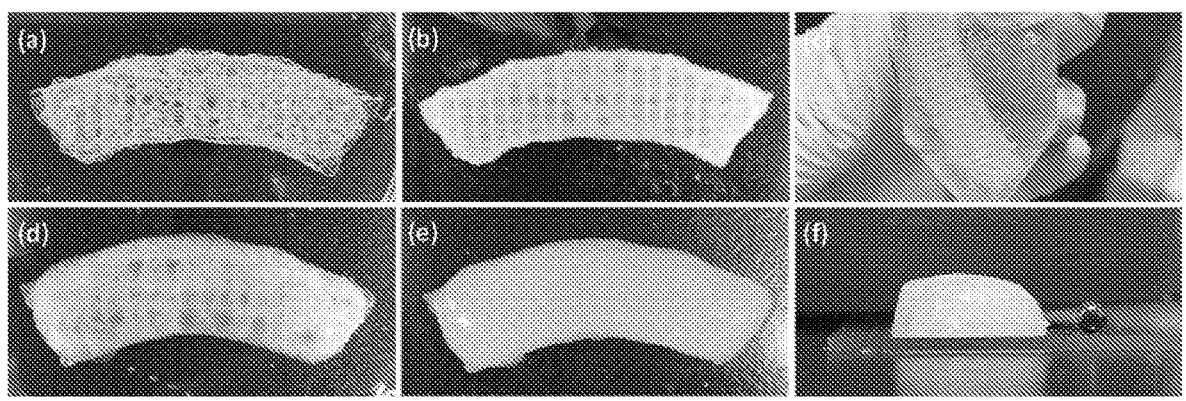
FIG. 11 shows printed chitosan-PVA mesh tissues and composite tissues with PVA added as a secondary addition. (a) Printed chitosan-PVA mesh with 12% infill, (b) partially dried mesh, (c) mesh in 20% PVA solution, (d) mesh with PVA matrix and final, freeze-thawed and hydrated composite (e) from above and (f) from the side. The diameter of the size reference ball is 2.4 mm (3/32").
Figure 13:
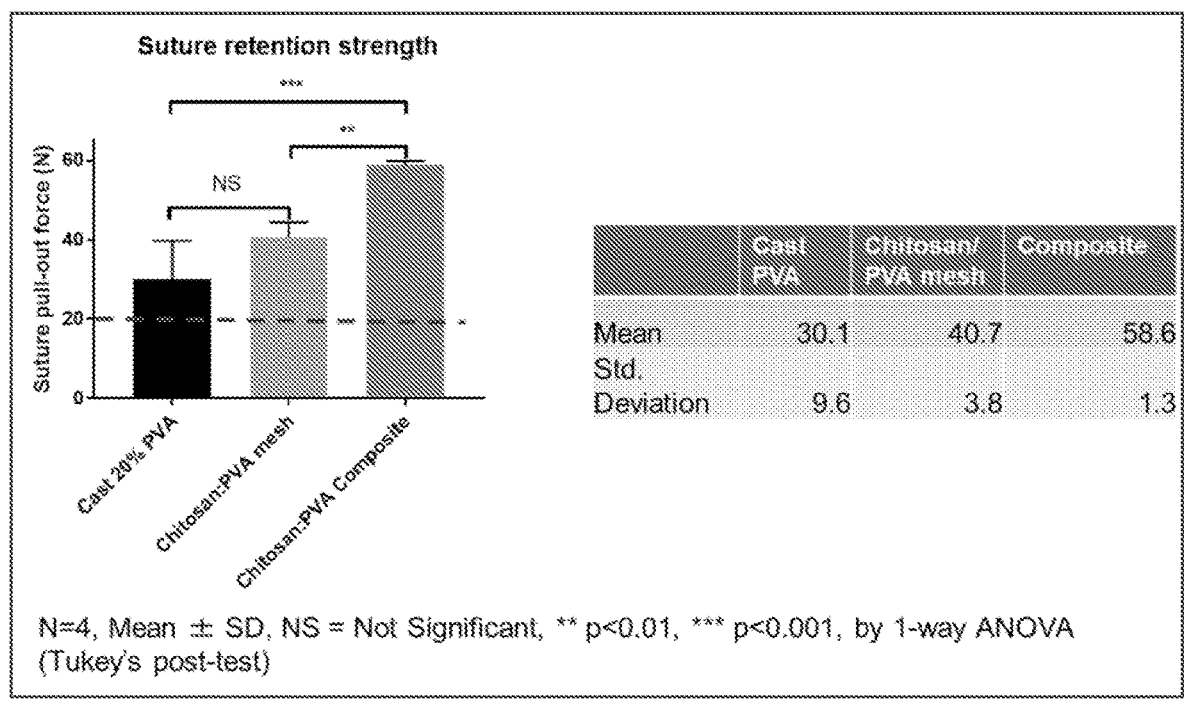
FIG. 13 shows the suture pull-out strength of printed, cast and composite chitosan:PVA tissues (red dashed line indicates target SPO value of 20N).

Printed chitosan:PVA mesh, cast PVA-only and composite chitosan:PVA mesh+cast PVA tissues were fabricated according to methods described above. All tissue types were similar dimensions and were compatible with the various mechanical testing protocols (FIG. 11). We hypothesized that the cast PVA component would increase the compressive strength of the printed mesh, and that the printed mesh would increase the suture retention strength of the cast PVA scaffold. To examine any synergistic interaction between the printed mesh and cast components of the tissues in detail, we performed direct comparisons of suture pull-out strength, indentation (compressive) strength, tensile strength and modulus for multiple replicates of printed (chitosan:PVA), composite (chitosan:PVA-PVA) and cast (PVA) tissues (FIGS. 12-15).

For suture pull-out (FIG. 12), our tests demonstrated that composite chitosan:PVA tissues have significantly increased suture pull-out strength (58.6±1.3N) vs printed-only tissues (40.7±3.8N, $p<0.01$ by ANOVA) or cast PVA-only tissues (30.1±9.6N, $p<0.001$), suggesting the printed fiber network and the cast PVA have a synergistic effect to increase suture retention strength. Although not specifically tested, we further hypothesize that circumferential-patterning of printed fibers will help to distribute compressive stresses appropriately throughout the meniscus tissue via so called "hoop stresses" similar to the biological meniscus.

For tissue indentation (compressive) strength (FIG. 13), we demonstrate that cast PVA (93.1±4.5 kPa) and chitosan:PVA composite (105.4±10.4 kPa) tissues both have significantly greater indentation strengths compared to printed-only tissues (23.9±2.4 kPa) ($p<0.0001$ by ANOVA). This data demonstrates that the secondary cast PVA matrix is contributing significantly to tissue indentation strength. The slight (non-significant) increase in indentation strength in the composite vs cast tissue may be due to the cast PVA in the composite being restricted to discreet "cells" within the rectilinear pattern of the printed fibers. This may restrict the expansion of the cast PVA when under compression and increase tissue stiffness, however this effect is hypothetical.

Figure 14:
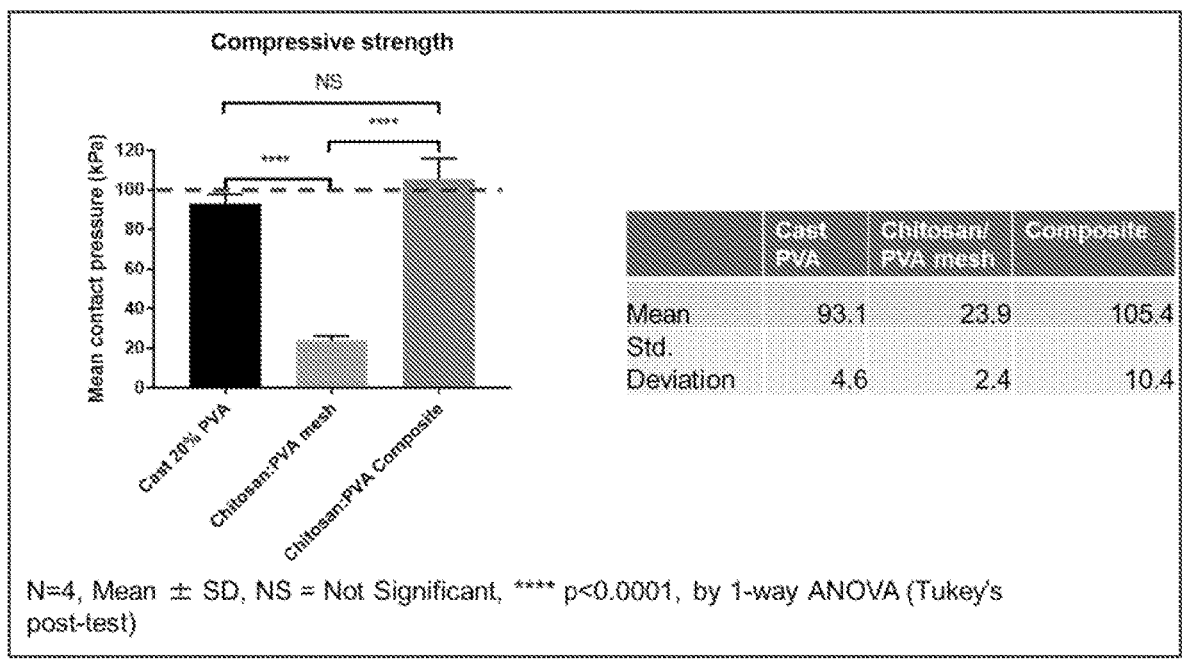
FIG. 14 shows the indentation (compressive) strength of printed, cast and composite tissues (red line indicates target indentation value of 100 kPa).
Figures 15, 16:
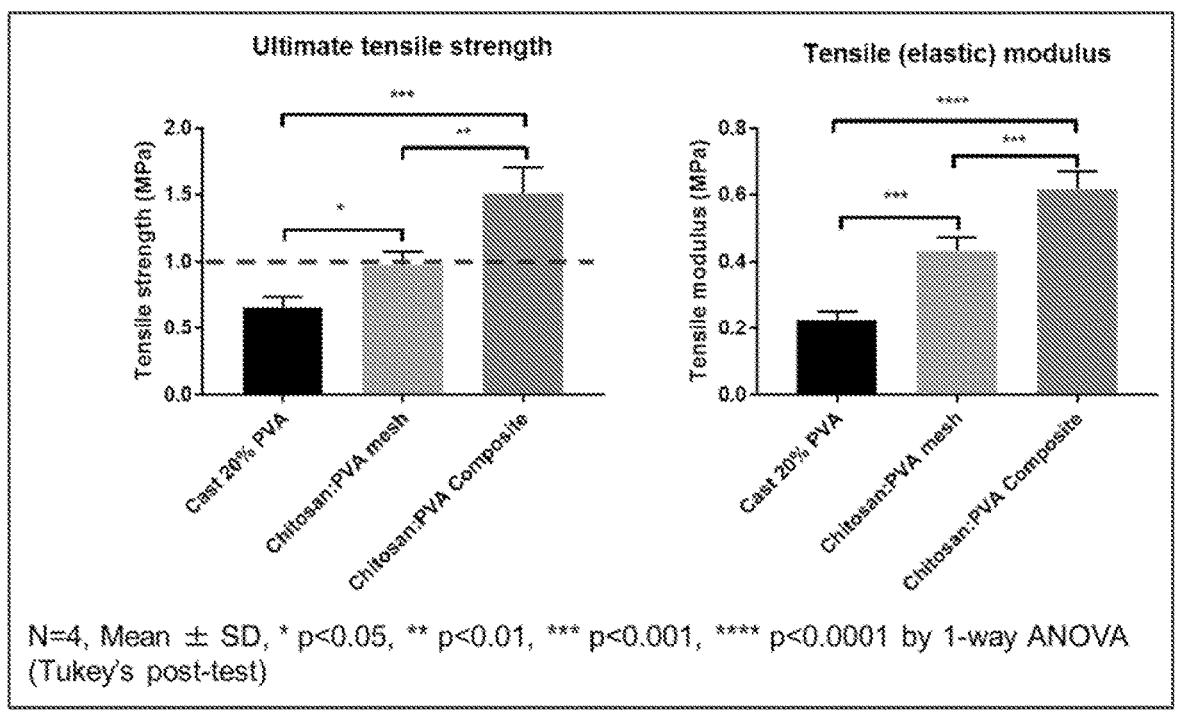
FIG. 15 shows the values for ultimate tissue tensile strength and tensile modulus in MPa.
FIG. 16 shows the ultimate tensile strength and tensile modulus of cast, printed and composite chitosan:PVA tissues (red line indicates target ultimate tensile strength value of 1 MPa).

The three tissue types, cast PVA, printed mesh and composite were also tested for ultimate tensile strength (breaking strength) and tensile modulus as a measure of tissue stiffness (FIGS. 14 & 15). Tests demonstrate that cast PVA tissues (0.66±0.08 MPa) are just over half of the required target tensile strength of 1 MPa and are significantly weaker than the printed-only tissues which are close to the target value at 0.98±0.1 MPa ($p<0.05$). The chitosan:PVA composite tissues have a significantly greater ultimate tensile strength of 1.52±0.2 MPa compared to both cast ($p<0.001$) and printed mesh tissues ($p<0.01$), again suggesting the printed mesh and secondary cast matrix components have a synergistic interaction resulting in a tissue with increased tensile strength. The tensile modulus of the three tissue types follows a similar pattern to the ultimate strength measurements, with cast tissue being the softest at 0.23±0.03 MPa, printed-only tissues significantly stiffer at 0.44±0.04 MPa ($p<0.01$) and composite tissues being significantly stiffer than printed mesh only ($p<0.001$) and cast PVA tissues ($p<0.0001$), with a tensile modulus of 0.62±0.05 MPa (Figures JJ & KK).

Discussion: Printed fibers of blended chitosan:PVA have particularly high elasticity and ultimate tensile strength, printed meniscus structures containing this blend are thus capable of resisting high tensile forces and suture pull-out forces, even at relatively low fiber in-fill densities of 7-15%. Unfortunately, the compressive strength of these printed structures was far below the target for this project, and the cadaver lab tests highlighted the importance of finding strategies to also solve the issue of delamination during surgical manipulation. The concept of combining printed fibers and cast secondary matrices was hypothesized as a potential method to simultaneously solve both limitations with CNC, PEGDA and PVA secondary matrices tested. Cast PVA hydrogels have previously demonstrated promise as a full meniscus replacement; small animal studies using PVA-based meniscal implants demonstrated a positive effect vs. meniscectomy controls in preventing articular cartilage damage in rabbits (Kobayashi, 2003), however studies in larger animals demonstrated that PVA hydrogel implants in sheep did not have a positive outcome when compared to meniscus allografts (Kelly, 2007), with regular failure of the grafts due to radial tears and extrusion from the knee joint. The authors concluded that the failure of these implants was not due to the use of PVA per-se, but was caused by; 1. Inappropriate sizing of the implants, 2. Inappropriate fixation of the implants, 3. An abrasive under surface, 4. The implants were isotropic and couldn't distribute hoop stresses in an appropriate way. Another concern with PVA hydrogels is the lack of porosity preventing cell engraftment, however a recent study has demonstrated that the inclusion of sodium hydrogen carbonate as a porogen can generate porous PVA meniscus implants that demonstrate improved fibrochondrocyte cellular ingrowth and engraftment in ex-vivo models (Coluccino, 2018).

We hypothesized that a composite approach with the inclusion of a custom-sized fiber scaffold with specific fiber orientation and high suture retention strength, with a secondary cast matrix, could remedy the limitations we highlighted in our studies, and the issues that led to graft failure in the Kelly study. The data we generated demonstrates that in the lab conditions we tested, combining chitosan:PVA mesh and a PVA or PEGDA secondary matrix, had an additive or in some cases synergistic effect on tissue mechanical performance.

The invention claimed is:

1. A meniscal implant comprising a plurality of layers deposited by a bioprinter, each layer comprising synthetic tissue fiber(s) comprising a solidified biocompatible matrix, wherein the solidified biocompatible matrix in at least one layer of the meniscal implant comprises a reinforced composite hydrogel, wherein the reinforced composite hydrogel comprises:
  (i) a hydrogel material selected from the group consisting of alginate and chitosan, wherein cross-linking of the hydrogel material occurs with printing; and
  (ii) at least one reinforcement material selected from the group consisting of polyethylene (glycol) diacrylate (PEGDA), poly (vinyl alcohol) (PVA), and combinations thereof, wherein the reinforcement material is blended with the hydrogel material and cross-linked either simultaneously or sequentially with printing to form a double network hydrogel.

2. The meniscal implant according to claim 1, wherein the hydrogel material comprises chitosan and the reinforcement material comprises PVA.

3. The meniscal implant according to claim 1, wherein the hydrogel material comprises alginate or chitosan and the reinforcement material comprises PEGDA.

4. The meniscal implant according to claim 3, wherein the hydrogel material comprises chitosan and the reinforcement material comprises PVA and PEGDA.

5. The meniscal implant according to claim 1, wherein the reinforcement material is PEGDA and addition and cross-linking of the reinforcement material occurs post-printing.

6. The meniscal implant according to claim 1, wherein a first reinforcement material is blended with the hydrogel material and cross-linked either simultaneously or sequentially with printing, and a second reinforcement material is added to the printed layers and crosslinked post-printing.

7. The meniscal implant according to claim 6, wherein the first reinforcement material is PVA and the second reinforcement material is PEGDA.

8. The meniscal implant according to claim 1, wherein the hydrogel material comprises between about 2.5% and 6% (w/v) chitosan, or about 4.5% (w/v) chitosan.

9. The meniscal implant according to claim 8, wherein the chitosan is cross-linked with a crosslinker comprising about 2.5% sodium tripolyphosphate (STP) and about 15% polyethylene glycol (PEG) 20 kDa.

10. The meniscal implant according to claim 9, wherein the reinforced composite hydrogel comprises about 4.5% (w/v) chitosan blended in a 1:1 ratio with about 15% PVA.

11. The meniscal implant according to claim 3, wherein the PEGDA has a molecular weight between about 1000 and 6000 Da, or about 3400 Da.

12. A method of making the meniscal implant of claim 1, comprising depositing synthetic tissue fiber(s) from a bioprinter to form a plurality of layers, each fiber comprising a solidified biocompatible matrix, wherein the solidified biocompatible matrix in at least one layer of the meniscal implant comprises a reinforced composite hydrogel comprising a hydrogel material selected from the group consisting of alginate and chitosan, and at least one reinforcement material selected from the group consisting of polyethylene (glycol) diacrylate (PEGDA), poly (vinyl alcohol) (PVA), and combinations thereof, wherein the at least one reinforcement material is cross-linked either simultaneously or sequentially with printing to form a double network hydrogel.

13. The method according to claim 12, wherein one or more layers of circumferentially-oriented synthetic tissue fiber(s) are alternated with one or more layers of radially-oriented synthetic tissue fiber(s).

14. The method according to claim 12, wherein the hydrogel material comprises chitosan and the reinforcement material comprises PVA.

15. The method according to claim 12, wherein the hydrogel material comprises alginate or chitosan and the reinforcement material comprises PEGDA.

16. The method according to claim 12, wherein the hydrogel material comprises chitosan and the reinforcement material comprises PVA and PEGDA.

17. The method according to claim 12, wherein the reinforcement material comprises PEGDA, and the method further comprises adding PEGDA to the layers and cross-linking the PEGDA after printing.

18. The method according to claim 12, wherein the reinforcement material comprises PVA, and the method further comprises blending the reinforcement material with the hydrogel material before printing and cross-linking the reinforcement material after printing.

19. The method according to claim 12 wherein a first reinforcement material is blended with the hydrogel material and cross-linked either simultaneously or sequentially with printing, and a second reinforcement material is added to the printed layers and crosslinked post-printing.

20. The method according to claim 19, wherein the method further comprises applying directional pressure to the second reinforcement material to increase infiltration of the second reinforcement material into the printed layers.

21. The method according to claim 19, wherein the infill density of the printed layers is less than 90%, 85%, 80%, 75%, 70%, 65%, 60%, 55%, 50%, 45% 40%, 35%, 30%, 25%, 20%, 15% or 10% before addition of the second reinforcement material.

22. The method according to claim 2, wherein the hydrogel material is chitosan, the first reinforcement material is PVA and the second reinforcement material is PEGDA.

23. The method according to claim 14, wherein the hydrogel material comprises between about 2.5% and 6% (w/v) chitosan, or about 4.5% (w/v) chitosan.

24. The method according to claim 23, wherein the chitosan is cross-linked with a crosslinker comprising about 2.5% sodium tripolyphosphate (STP) and about 15% polyethylene glycol (PEG) 20 kDa.

25. The method according to claim 14, wherein the reinforced composite hydrogel comprises about 4.5% (w/v) chitosan blended in a 1:1 ratio with about 15% PVA.

26. The method according to claim 15, wherein the reinforced composite hydrogel comprises alginate or chitosan and a PEGDA having a molecular weight between about 1000 and 6000 Da, or about 3400 Da.

27. The method according to claim 26, wherein the PEGDA is crosslinked with ammonium persulfate (APS) and tetramethylethylenediamine (TEMED).

28. A meniscal implant comprising a plurality of layers deposited by a bioprinter, each layer comprising synthetic tissue fiber(s) comprising a solidified biocompatible matrix, wherein the solidified biocompatible matrix in at least one layer of the meniscal implant comprises a reinforced composite hydrogel wherein the reinforced composite hydrogel comprises a hydrogel material selected from the group consisting of alginate and chitosan, a first reinforcement material blended with the hydrogel material and cross-linked simultaneously or sequentially with printing, and a second reinforcement material added and cross-linked post-printing, wherein the first and second reinforcement material are the same and comprise PVA or wherein the first reinforcement material comprises PVA and the second reinforcement material comprises PEGDA and wherein a double network hydrogel is formed.

* * * * *